(12) United States Patent
Long et al.

(10) Patent No.: US 7,828,791 B2
(45) Date of Patent: Nov. 9, 2010

(54) MEDICAL INSTRUMENT HAVING A GUIDEWIRE AND ARTICULATED CATHETER

(75) Inventors: Gary L. Long, Cincinnati, OH (US); Gregory J. Bakos, Mason, OH (US); Omar J. Vakharia, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 46 days.

(21) Appl. No.: 11/128,072

(22) Filed: May 12, 2005

(65) Prior Publication Data

US 2005/0256507 A1 Nov. 17, 2005

Related U.S. Application Data

(60) Provisional application No. 60/571,026, filed on May 14, 2004, provisional application No. 60/571,118, filed on May 14, 2004.

(51) Int. Cl.
*A61M 25/01* (2006.01)
(52) U.S. Cl. .................... 604/528; 606/108
(58) Field of Classification Search .......... 604/528; 606/117, 118, 129, 141, 144, 146, 113; 600/146
See application file for complete search history.

(56) References Cited

U.S. PATENT DOCUMENTS

| | | | |
|---|---|---|---|
| 1,891,054 A | 12/1932 | Pitman | |
| 3,892,228 A | 7/1975 | Mitsui | |
| 4,176,662 A | 12/1979 | Frazer | |
| 4,207,872 A | 6/1980 | Meiri et al. | |
| 4,224,929 A | 9/1980 | Furihata | |
| 4,326,530 A | 4/1982 | Fleury, Jr. | |
| 4,447,227 A | 5/1984 | Kotsanis | |
| 4,686,965 A | 8/1987 | Bonnet et al. | |
| 4,854,325 A | 8/1989 | Stevens | |
| 4,875,489 A | 10/1989 | Messner et al. | |
| 4,947,827 A | 8/1990 | Opie et al. | |

(Continued)

FOREIGN PATENT DOCUMENTS

EP 0667115 A1 1/1995

(Continued)

OTHER PUBLICATIONS

Applegate, M.N. et al., "The measurement of forces exerted during colonoscopy," Gastrointestinal Endoscopy, vol. 52, No. 2, pp. 237-240 (Aug. 2000).

(Continued)

*Primary Examiner*—Nicholas D Lucchesi
*Assistant Examiner*—Laura A Bouchelle

(57) ABSTRACT

A first medical instrument includes a flexible catheter and a medical guidewire extendable beyond a distal end of the catheter. The catheter has an articulated section. The medical guidewire has first and second segments, wherein the bending moment of inertia of the first segment is less than the bending moment of inertia of the second segment. A second medical instrument includes a flexible catheter, a mechanized guidewire assembly, and a medical guidewire extendable beyond a distal end of the catheter. The catheter has an articulated section. The medical guidewire has an exterior surface including a repetitive series of spaced-apart surface elevation features. One example of surface elevation features is external threads. The spaced-apart surface elevation features are adapted for operable engagement with the mechanized guidewire drive assembly.

20 Claims, 25 Drawing Sheets

U.S. PATENT DOCUMENTS

| | | | |
|---|---|---|---|
| 5,025,778 A | 6/1991 | Silverstein et al. | |
| 5,078,716 A | 1/1992 | Doll | |
| 5,113,872 A | 5/1992 | Jahrmarkt et al. | |
| 5,135,483 A | 8/1992 | Wagner et al. | |
| 5,154,164 A | 10/1992 | Chikama | |
| 5,217,001 A | 6/1993 | Nakao et al. | |
| 5,337,732 A | 8/1994 | Grundfest et al. | |
| 5,345,925 A | 9/1994 | Allred, III et al. | |
| 5,360,403 A | 11/1994 | Mische | |
| 5,363,847 A | 11/1994 | Viera | |
| 5,398,670 A | 3/1995 | Stubbs et al. | |
| 5,431,645 A | 7/1995 | Smith et al. | |
| 5,489,256 A | 2/1996 | Adair | |
| 5,503,616 A | 4/1996 | Jones | |
| 5,505,686 A * | 4/1996 | Willis et al. | 600/104 |
| 5,522,819 A | 6/1996 | Graves et al. | |
| 5,575,754 A | 11/1996 | Konomura | |
| 5,584,843 A * | 12/1996 | Wulfman et al. | 606/159 |
| 5,595,565 A | 1/1997 | Trimmer | |
| 5,604,531 A | 2/1997 | Iddan et al. | |
| 5,643,175 A | 7/1997 | Adair | |
| 5,645,519 A | 7/1997 | Lee et al. | |
| 5,730,704 A | 3/1998 | Avitall | |
| 5,749,889 A | 5/1998 | Bacich et al. | |
| 5,782,855 A | 7/1998 | Lau et al. | |
| 5,836,947 A | 11/1998 | Fleishmann et al. | |
| 5,882,293 A | 3/1999 | Ouchi | |
| 5,891,055 A | 4/1999 | Sauter | |
| 5,895,417 A | 4/1999 | Anderson et al. | |
| 5,904,648 A | 5/1999 | Arndt et al. | |
| 5,944,654 A | 8/1999 | Crawford | |
| 5,984,860 A | 11/1999 | Shan | |
| 6,007,482 A | 12/1999 | Madni et al. | |
| 6,036,636 A | 3/2000 | Konomura | |
| 6,059,719 A | 5/2000 | Yamamoto et al. | |
| 6,080,171 A | 6/2000 | Keith et al. | |
| 6,106,488 A | 8/2000 | Vogel et al. | |
| 6,152,918 A | 11/2000 | Padilla et al. | |
| 6,162,171 A | 12/2000 | Ng et al. | |
| 6,171,234 B1 | 1/2001 | White et al. | |
| 6,190,382 B1 * | 2/2001 | Ormsby et al. | 606/33 |
| 6,203,525 B1 | 3/2001 | Whayne et al. | |
| 6,238,389 B1 | 5/2001 | Paddock | |
| 6,241,702 B1 | 6/2001 | Lundquist | |
| 6,309,346 B1 | 10/2001 | Farhadi | |
| 6,346,106 B1 | 2/2002 | Jako | |
| 6,352,503 B1 | 3/2002 | Matsui | |
| 6,355,034 B2 | 3/2002 | Cosmescu | |
| 6,359,379 B1 | 3/2002 | Lee et al. | |
| 6,371,928 B1 | 4/2002 | Mcfann | |
| 6,454,758 B1 | 9/2002 | Thompson et al. | |
| 6,527,753 B2 | 3/2003 | Sekine et al. | |
| 6,554,793 B1 | 4/2003 | Pauker et al. | |
| 6,569,085 B2 | 5/2003 | Kortenbach et al. | |
| 6,572,526 B1 | 6/2003 | Ford | |
| 6,689,130 B2 | 2/2004 | Arai et al. | |
| 6,699,180 B2 | 3/2004 | Kobayashi | |
| 6,740,030 B2 | 5/2004 | Martone et al. | |
| 6,770,027 B2 | 8/2004 | Banik et al. | |
| 6,814,727 B2 | 11/2004 | Mansouri-Ruiz | |
| 7,331,243 B2 | 2/2008 | Pfeffer | |
| 2001/0025171 A1 | 9/2001 | Mortier et al. | |
| 2002/0010426 A1 | 1/2002 | Vandenbroek et al. | |
| 2002/0026156 A1 | 2/2002 | Quinn | |
| 2002/0107506 A1 | 8/2002 | McGuckin | |
| 2002/0107530 A1 | 8/2002 | Sauer et al. | |
| 2002/0151889 A1 | 10/2002 | Swanson et al. | |
| 2002/0161393 A1 | 10/2002 | Krolik | |
| 2002/0183591 A1 | 12/2002 | Matsuura et al. | |
| 2003/0036679 A1 | 2/2003 | Kortenbach et al. | |
| 2003/0040737 A1 | 2/2003 | Merril et al. | |
| 2003/0097099 A1 | 5/2003 | Quinn | |
| 2003/0171651 A1 | 9/2003 | Page et al. | |
| 2003/0176880 A1 | 9/2003 | Long et al. | |
| 2003/0229269 A1 | 12/2003 | Humphrey | |
| 2004/0111019 A1 | 6/2004 | Long et al. | |
| 2004/0111020 A1 | 6/2004 | Long et al. | |
| 2004/0199052 A1 * | 10/2004 | Banik et al. | 600/142 |
| 2004/0199087 A1 | 10/2004 | Swain et al. | |
| 2004/0199088 A1 | 10/2004 | Bakos et al. | |
| 2004/0230095 A1 | 11/2004 | Stefanchik et al. | |
| 2004/0230096 A1 | 11/2004 | Stefanchik et al. | |
| 2005/0055086 A1 | 3/2005 | Stobie | |
| 2005/0085851 A1 | 4/2005 | Fiehler et al. | |
| 2005/0250989 A1 | 11/2005 | Suzuki | |
| 2005/0256505 A1 | 11/2005 | Long et al. | |
| 2005/1025642 | 11/2005 | Long et al. | |
| 2005/0272976 A1 | 12/2005 | Tanaka et al. | |
| 2006/0173239 A1 | 8/2006 | Neumann et al. | |

FOREIGN PATENT DOCUMENTS

| | | |
|---|---|---|
| EP | 0827712 | 3/1998 |
| EP | 1284120 A1 | 2/2003 |
| EP | 1400205 | 3/2004 |
| FR | 2481915 | 11/1981 |
| GB | 2032278 | 5/1980 |
| JP | 56-8028 | 1/1981 |
| WO | WO 91/14391 | 10/1991 |
| WO | WO 94/05200 | 3/1994 |
| WO | WO 97/29680 | 8/1997 |
| WO | WO 97/41767 | 11/1997 |
| WO | WO 98/11816 | 3/1998 |
| WO | WO 98/19608 A1 | 5/1998 |
| WO | WO 99/27840 | 6/1999 |
| WO | WO 99/30610 | 6/1999 |
| WO | WO 99/32028 | 7/1999 |
| WO | WO 99/34726 | 7/1999 |
| WO | WO 99/53827 | 10/1999 |
| WO | WO 00/48506 A1 | 2/2000 |
| WO | WO 00/22975 | 4/2000 |
| WO | WO 00/44275 | 8/2000 |
| WO | WO 01/49165 A1 | 1/2001 |
| WO | WO 01/08548 | 2/2001 |
| WO | WO 01/67967 | 9/2001 |
| WO | 03/053505 | 7/2003 |

OTHER PUBLICATIONS

Office Action, U.S. Appl. No. 11/128,023 entitled "Medical Instrument Having a Controlled Guidewire Drive" (Jun. 28, 2006).
Office Action, U.S. Appl. No. 11/128,023 entitled "Medical Instrument Having a Controlled Guidewire Drive" (Oct. 5, 2006).
Office Action, U.S. Appl. No. 11/128,023 entitled "Medical Instrument Having a Controlled Guidewire Drive" (Mar. 26, 2007).
Office Action, U.S. Appl. No. 11/128,023 entitled "Medical Instrument Having a Controlled Guidewire Drive" (Aug. 22, 2007).
Office Action, U.S. Appl. No. 11/128,023 entitled "Medical Instrument Having a Controlled Guidewire Drive" (Jan. 24, 2008).
Office Action, U.S. Appl. No. 11/128,023 entitled "Medical Instrument Having a Controlled Guidewire Drive" (Mar. 5, 2009).
Office Action, U.S. Appl. No. 11/128,036 entitled "Medical Instrument Having a Medical Guidewire" (Jun. 27, 2006).
Office Action, U.S. Appl. No. 11/128,036 entitled "Medical Instrument Having a Medical Guidewire" (Mar. 7, 2007).
Office Action, U.S. Appl. No. 11/128,036 entitled "Medical Instrument Having a Medical Guidewire" (Jun. 6, 2008).
Notice of Allowance, U.S. Appl. No. 11/128,036 entitled "Medical Instrument Having a Medical Guidewire" (Feb. 6, 2009).
Office Action, U.S. Appl. No. 11/128,108 entitled "Medical Instrument Having a Guidewire and an Add-to-Catheter" (Apr. 5, 2007).
Office Action, U.S. Appl. No. 11/128,108 entitled "Medical Instrument Having a Guidewire and an Add-to-Catheter" (Nov. 14, 2007).

Advisory Action, U.S. Appl. No. 11/128,108 entitled "Medical Instrument Having a Guidewire and an Add-to-Catheter" (Mar. 4, 2008).

Office Action, U.S. Appl. No. 11/128,108 entitled "Medical Instrument Having a Guidewire and an Add-to-Catheter" (May 14, 2008).

Office Action, U.S. Appl. No. 11/128,108 entitled "Medical Instrument Having a Guidewire and an Add-to-Catheter" (Dec. 2, 2008).

Advisory Action, U.S. Appl. No. 11/128,108 entitled "Medical Instrument Having a Guidewire and an Add-to-Catheter" (Feb. 18, 2009).

Office Action, U.S. Appl. No. 11/128,012 entitled "Medical Instrument Having a Catheter and a Medical Guidewire" (Jun. 28, 2006).

Office Action, U.S. Appl. No. 11/128,012 entitled "Medical Instrument Having a Catheter and a Medical Guidewire" (Oct. 5, 2006).

Office Action, U.S. Appl. No. 11/128,012 entitled "Medical Instrument Having a Catheter and a Medical Guidewire" (Mar. 26, 2007).

Office Action, U.S. Appl. No. 11/128,012 entitled "Medical Instrument Having a Catheter and a Medical Guidewire" (Feb. 8, 2008).

Office Action, U.S. Appl. No. 11/128,012 entitled "Medical Instrument Having a Catheter and a Medical Guidewire" (Mar. 4, 2009).

Office Action, U.S. Appl. No. 11/089,181 entitled "Device to Measure Insertion Force" (Jun. 3, 2008).

Appleyard, M.N. et al., "The Measurement of forces exerted during colonoscopy," Gastrointestinal Endoscopy, vol. 52, No. 2, pp. 237-240 (Aug. 2000).

Mosse, C.A. et al., "Device for measuring the forces exerted on the shaft of an endoscope during colonoscopy," *Medical & Biological Engineering & Computing*, p. 186-190 (Mar. 1998).

International Preliminary Report on Patentability, International Application No. PCT/US2005/016759 (7 pages) (Sep. 22, 2008).

International Preliminary Report on Patentability, International Application No. PCT/US2005/016761 (3 pages) (Feb. 7, 2007).

International Preliminary Report on Patentability, International Application No. PCT/US2005/016858 (3 pages) (Mar. 1, 2007).

International Preliminary Report on Patentability, International Application No. PCT/US2005/016856 (3 pages) (Aug. 16, 2007).

Written Opinion, International Application No. PCT/US2005/016760 (3 pages) (Jul. 23, 2008).

International Preliminary Report on Patentability, International Application No. PCT/US2005/016856 (3 pages) (Jun. 14, 2007).

* cited by examiner

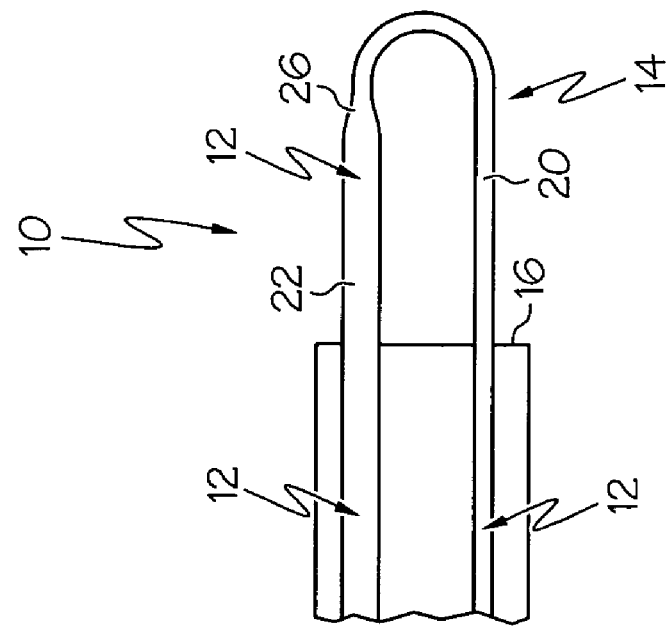
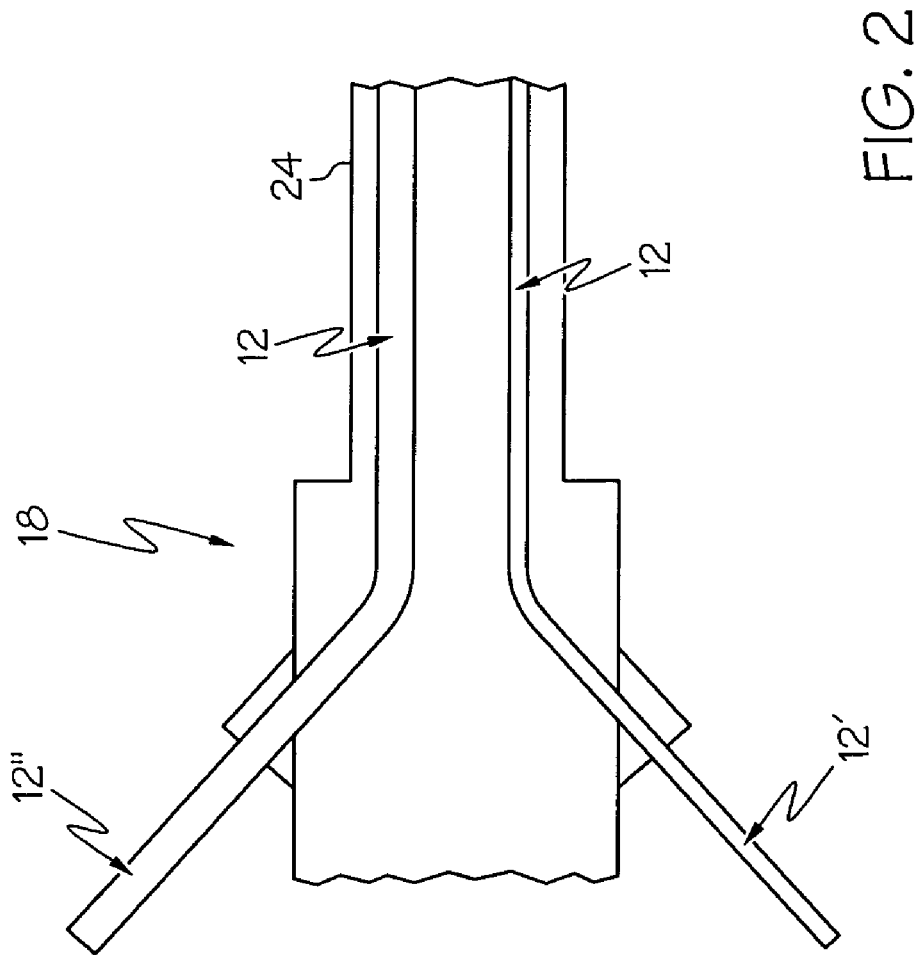
FIG. 2

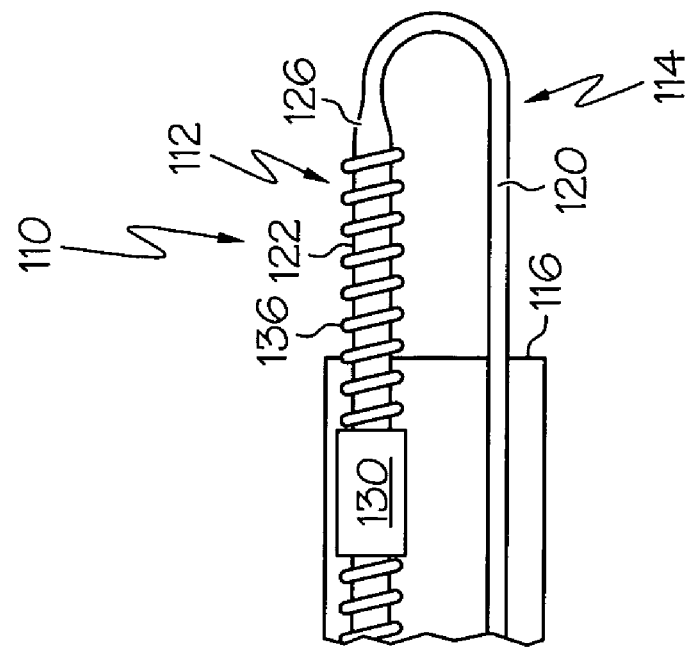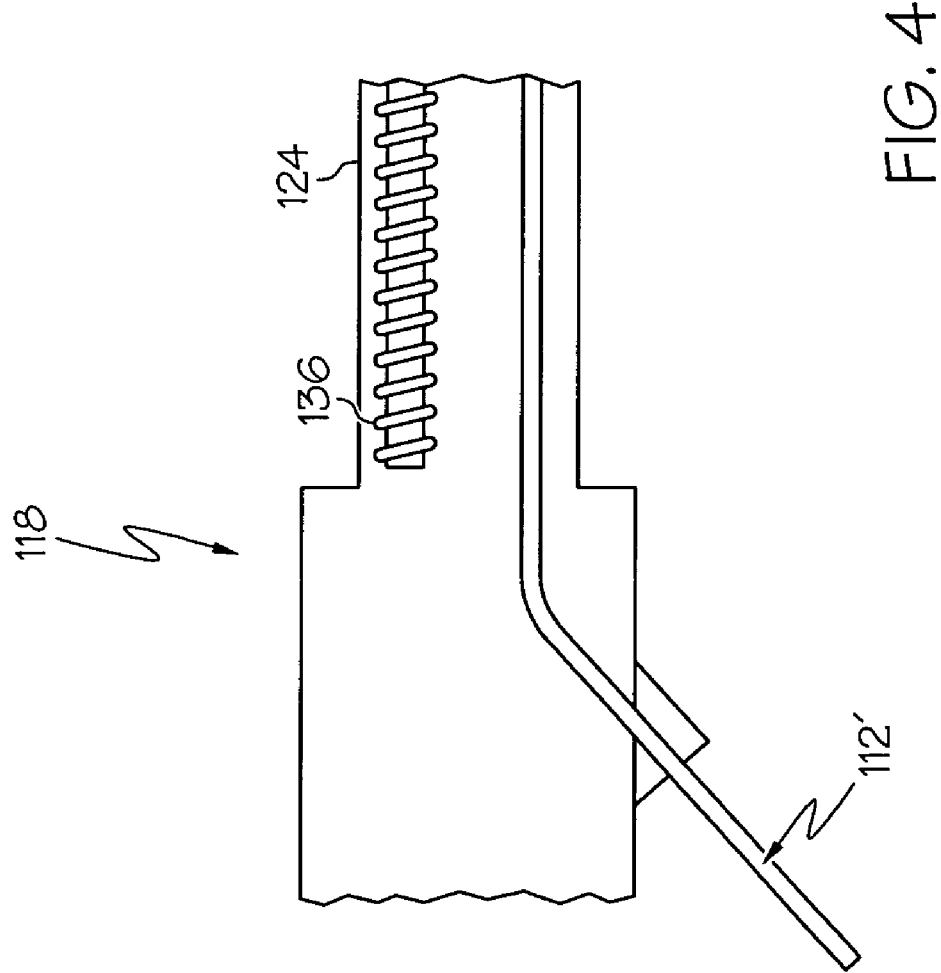
FIG. 4

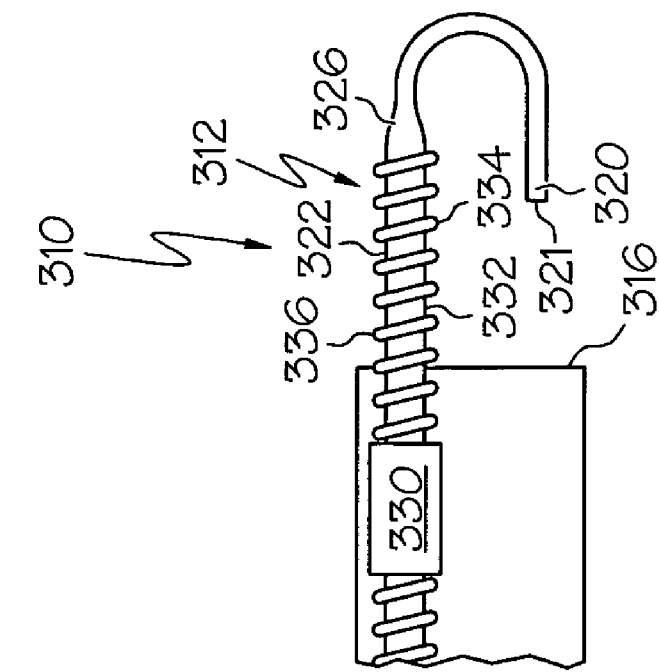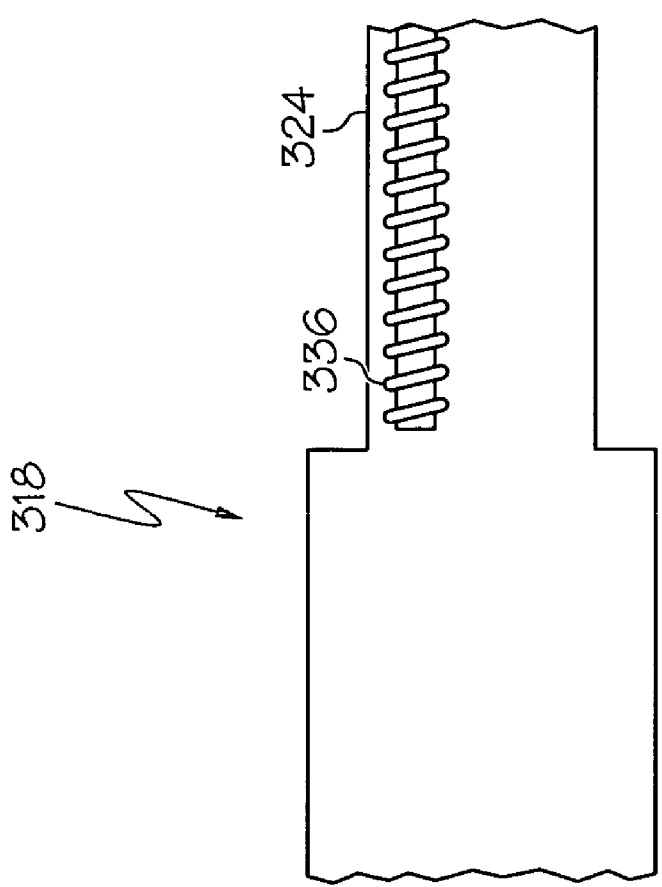
FIG. 7

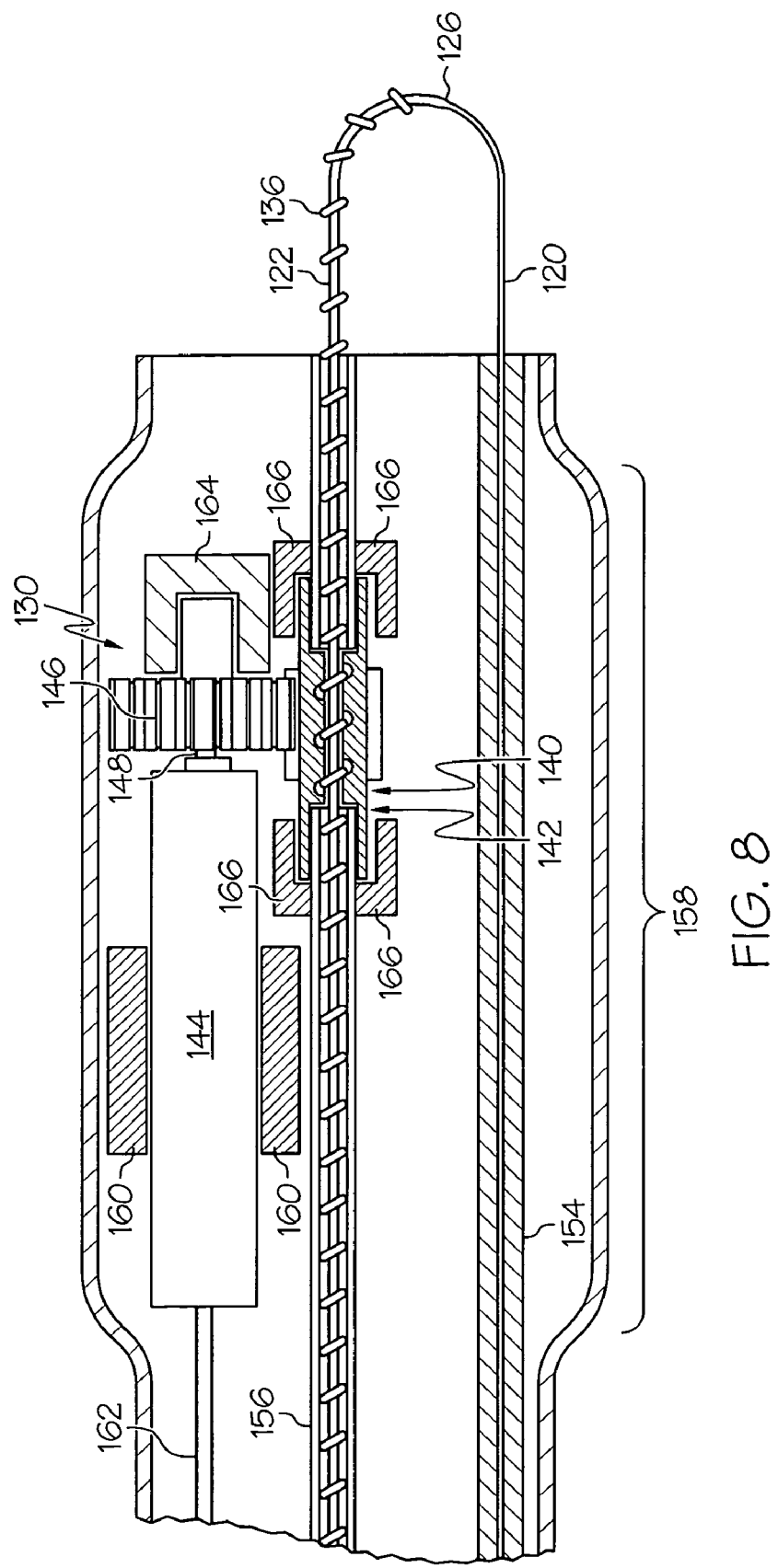

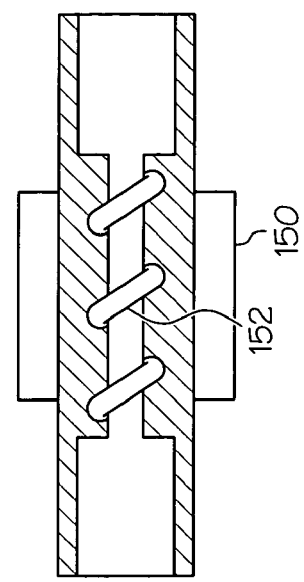
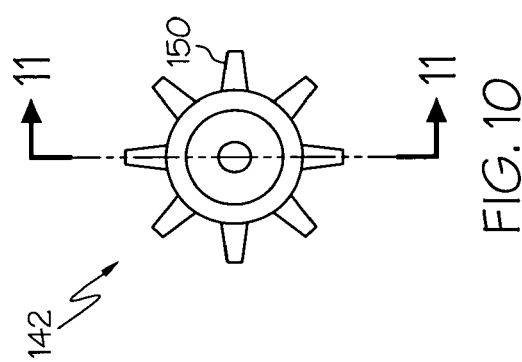
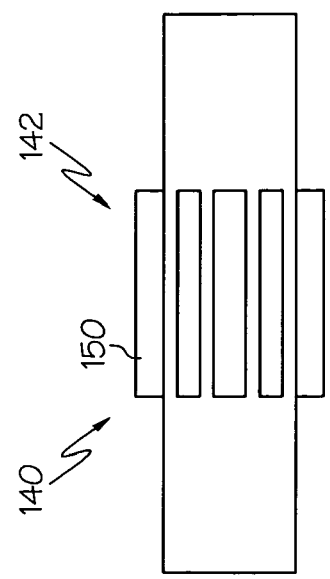

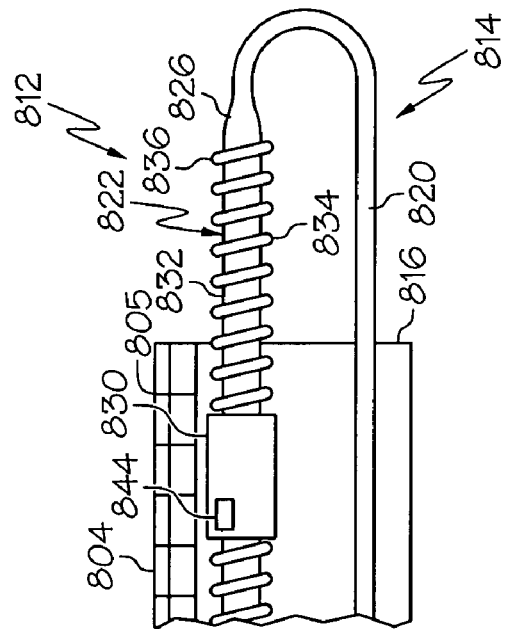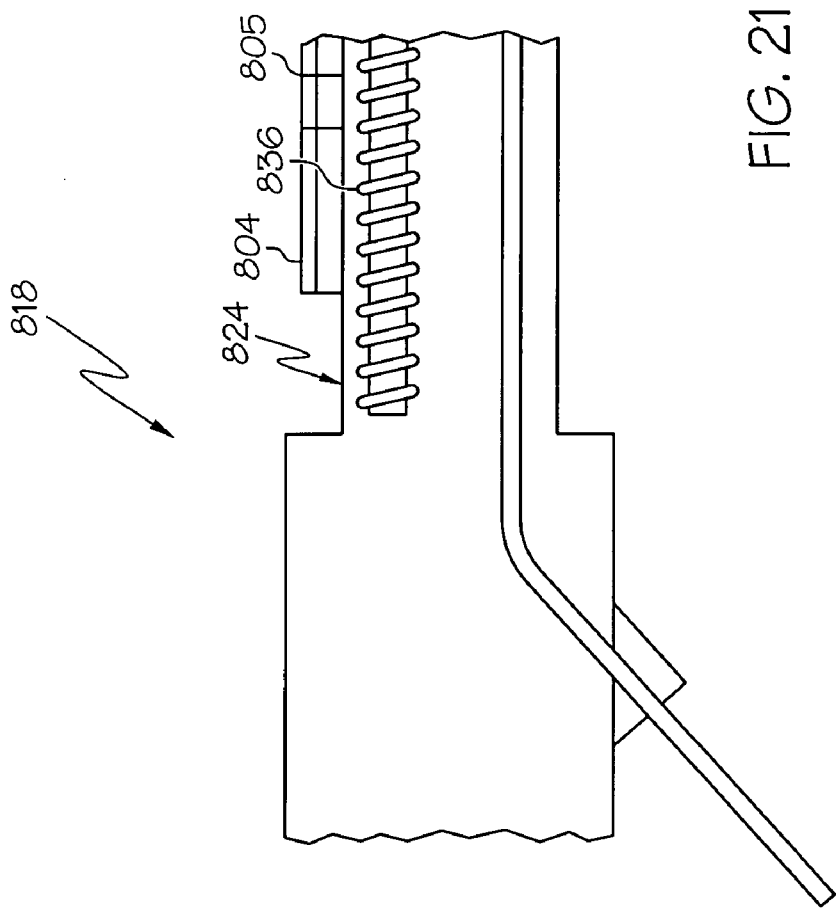
FIG. 21

//! PAGE START
MEDICAL INSTRUMENT HAVING A GUIDEWIRE AND ARTICULATED CATHETER

CROSS REFERENCE TO RELATED PATENT APPLICATIONS

This patent application claims priority of U.S. Provisional Application Ser. No. 60/571,026 filed May 14, 2004 and U.S. Provisional Application Ser. No. 60/571,118 filed May 14, 2004, the entire disclosures of which are incorporated herein by reference.

This patent application incorporates by reference: U.S. patent application Publication 2004/0111019 published Jun. 10, 2004; U.S. patent application Publication 2004/0111020 published Jun. 10, 2004; U.S. patent application Publication 2004/0199087 published Oct. 7, 2004; U.S. patent application Publication 2004/0199088 published Oct. 7, 2004; and U.S. patent application Publication 2004/0230096 published Nov. 18, 2004.

FIELD OF THE INVENTION

The present invention is related generally to medical instruments, and more particularly to a medical instrument having a medical guidewire.

BACKGROUND OF THE INVENTION

A physician typically accesses and visualizes tissue within a patient's gastrointestinal (GI) tract with a long, flexible endoscope. For the upper GI, a physician may insert a gastroscope into the sedated patient's mouth to examine and treat tissue in the esophagus, stomach, and proximal duodenum. For the lower GI, a physician may insert a colonoscope through the sedated patient's anus to examine the rectum and colon. Some endoscopes have a working channel, typically about 2.5-3.5 millimeters in diameter, extending from a port in the handpiece to the distal portion of the flexible insertion tube. A physician may insert medical devices into the working channel to help diagnose or treat tissues within the patient. Physicians commonly take tissue biopsies from the mucosal lining of the GI tract using a flexible, biopsy forceps through the working channel of the endoscope.

Insertion of a flexible endoscope, especially into the colon, can be a very time-consuming and uncomfortable procedure for the patient, even when sedated with drugs. A physician often needs several minutes to push a flexible endoscope through the convoluted sigmoid, descending, transverse, and ascending portions of the colon. The physician may diagnose and/or treat tissues within the colon either during insertion or removal of the endoscope. The flexible endoscope may "loop" within the colon, such as at the sigmoid colon or at the splenic flexure of the colon, so that it becomes difficult to further advance the endoscope along the colon. When a loop is formed, the force exerted to push the scope stretches the mesentery and causes pain for the patient. Depending on the anatomy of the patient and the skill of the physician in manipulating the flexible endoscope, some portions of the colon may be unexamined, thus increasing the risk of undiagnosed disease.

Guidewires have been used to aid the introduction of catheters and other instruments into many sites in the human body. Many medical applications and specific designs of guidewires have been for cardiovascular use. There are, however, specific challenges relates to the use of guidewires in the GI tract, as opposed to the vascular system. Thus, the bowel is more tortuous, softer and generally of larger diameter. Furthermore, in the case of the small intestine and the colon, these are longer than most arteries or veins.

Still, scientists and engineers continue to seek improved medical instruments having a medical guidewire.

SUMMARY

A first expression of an embodiment of the invention is for a medical instrument which includes a flexible catheter and a medical guidewire The catheter has a distal end and an articulated section insertable into a body lumen of a patient, wherein the articulated section is adapted to be controlled from outside the body lumen. The medical guidewire includes a working portion which is extendable as a loop track beyond the distal end of the catheter. The working portion has a maximum loop-track length and includes first and second segments together having a length greater than ninety percent of the maximum loop-track length. The first segment has a first bending moment of inertia and the second segment has a second bending moment of inertia, wherein the first bending moment of inertia is less than the second bending moment of inertia.

A second expression of an embodiment of the invention is for a medical instrument which includes a flexible catheter, a mechanized guidewire drive assembly, and a medical guidewire. The catheter has a distal end and an articulated section insertable into a body lumen of a patient, wherein the articulated section is adapted to be controlled from outside the body lumen. The medical guidewire includes a working portion which is extendable as a loop track beyond the distal end of the catheter. The working portion includes an exterior surface having a repetitive series of spaced-apart surface elevation features adapted for operable engagement with the mechanized guidewire drive assembly.

A first expression of an alternate embodiment of the invention is for a medical instrument which includes a flexible catheter and a medical guidewire. The catheter has a distal end and an articulated section insertable into a body lumen of a patient, wherein the articulated section is adapted to be controlled from outside the body lumen. The medical guidewire is extendable beyond the distal end of the catheter. The medical guidewire includes first and second segments. The first segment has a first bending moment of inertia and the second segment has a second bending moment of inertia, wherein the first bending moment of inertia is less than the second bending moment of inertia. The first segment has a free end which extends beyond the distal end of the catheter when the medical guidewire is fully extended.

A second expression of an alternate embodiment of the invention is for a medical instrument which includes a flexible catheter, a mechanized guidewire drive assembly, and a medical guidewire. The catheter has a distal end and an articulated section insertable into a body lumen of a patient, wherein the articulated section is adapted to be controlled from outside the body lumen. The medical guidewire is extendable beyond the distal end of the catheter. The medical guidewire includes an exterior surface having a repetitive series of spaced-apart surface elevation features adapted for operable engagement with the mechanized guidewire drive assembly. The medical guidewire has a free end which extends beyond the distal end of the catheter when the medical guidewire is fully extended.

Several benefits and advantages are obtained from one or more of the expressions and embodiments of the invention. In one application, having a medical instrument with an articulated catheter and with a loop-track or non-loop-track guidewire including a first segment having a bending moment of inertia less than that of a second segment allows easier extension of the first segment in a body lumen of a patient followed by easier extension and temporary anchoring of the second segment and easier advancement of the catheter, as can be appreciated by the artisan. In the same or a different application, having a medical instrument with an articulated catheter and with a loop-track or non-loop-track guidewire including an exterior surface having a repetitive series of spaced-apart surface elevation features, such as external threads, allows operable engagement thereof with a mechanized guidewire drive assembly for improved guidewire extension and catheter advancement, as can be appreciated by those skilled in the art. In one employment which utilizes a mechanized guidewire drive assembly, when the surface-elevation-feature engaging component of the mechanized guidewire drive assembly is located proximate the distal end of the catheter (insertion tube) of a flexible endoscope, there is less tendency for the catheter to "loop" within the colon and cause pain to the patient during a colonoscopy.

BRIEF DESCRIPTION OF THE FIGURES

FIG. 2 is a schematic side-elevational cutaway view of the guidewire structure of FIG. 1, with the sleeve omitted for clarity, employed in a first embodiment of a medical instrument having a catheter;

FIG. 4 is a schematic side-elevational cutaway view of the guidewire structure of FIG. 3, with the sleeve omitted for clarity, employed in a second embodiment of a medical instrument having a catheter;

FIG. 7 is a schematic side-elevational cutaway view of an alternate second embodiment of a guidewire structure, with the sleeve omitted for clarity, employed in an alternate second embodiment of a medical instrument having a catheter;

FIG. 8 is a more detailed view of a distal portion of the catheter of FIG. 4 showing a particular embodiment of the mechanized guidewire drive assembly including a motor, a spur gear, and a nut gear;

FIG. 9 is an exterior side-elevational view of the nut gear of FIG. 8;

FIG. 10 is an exterior front-elevational view of the nut gear of FIG. 9;

FIG. 11 is a cross-sectional view of the nut gear taken along lines 11-11 of FIG. 10;

FIG. 21 is a schematic side-elevational cutaway view of a seventh embodiment of a medical instrument of the invention including a loop-track guidewire and an add-to catheter having a rail;

Figure 22:
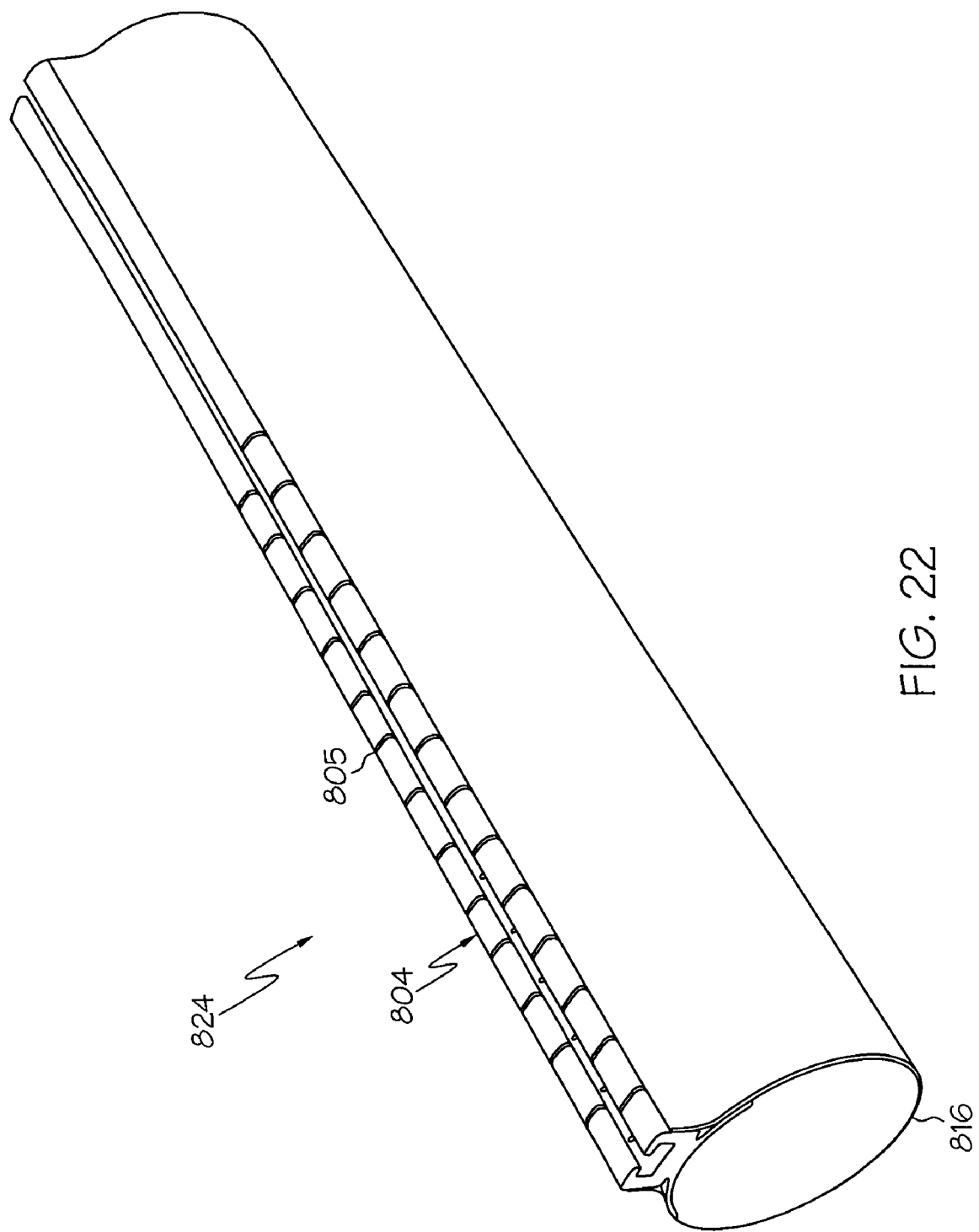
FIG. 22 is a perspective view of the catheter of FIG. 21 showing the notches in the rail of the catheter and with the guidewire and the guidewire passageway opening(s) omitted for clarity.
Figure 23:
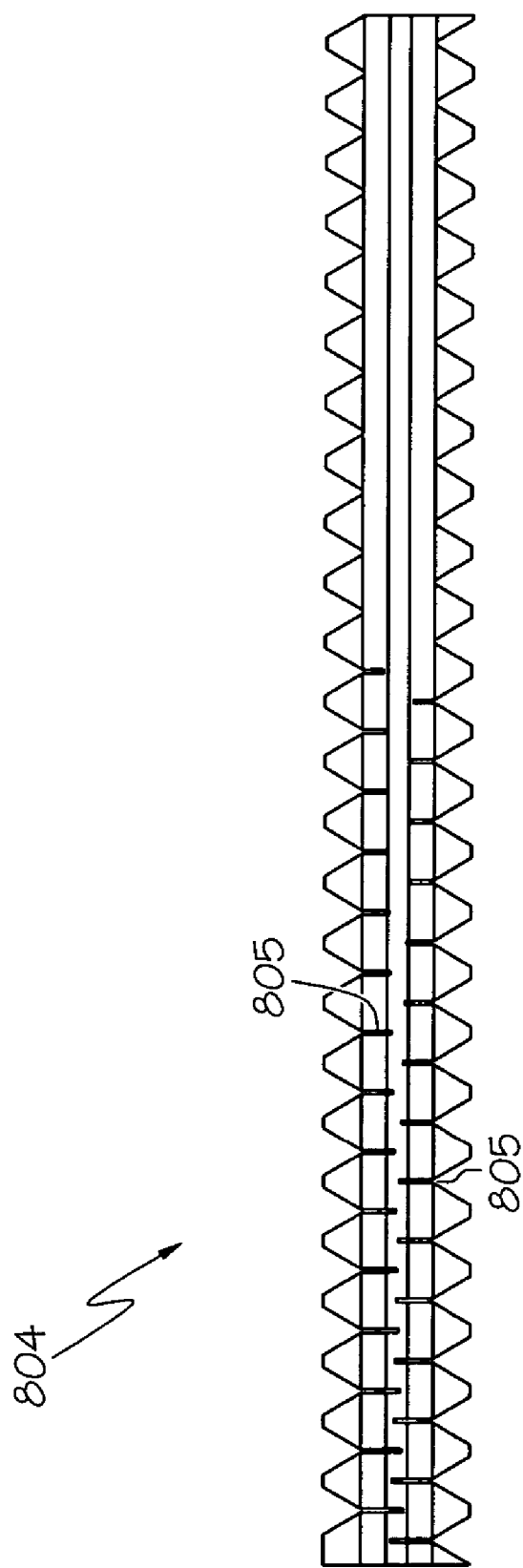
FIG. 23 is a more-detailed top planar view of the rail of FIG. 22, wherein the rail has been laid open to show the transverse extent of the notches.
Figure 24:
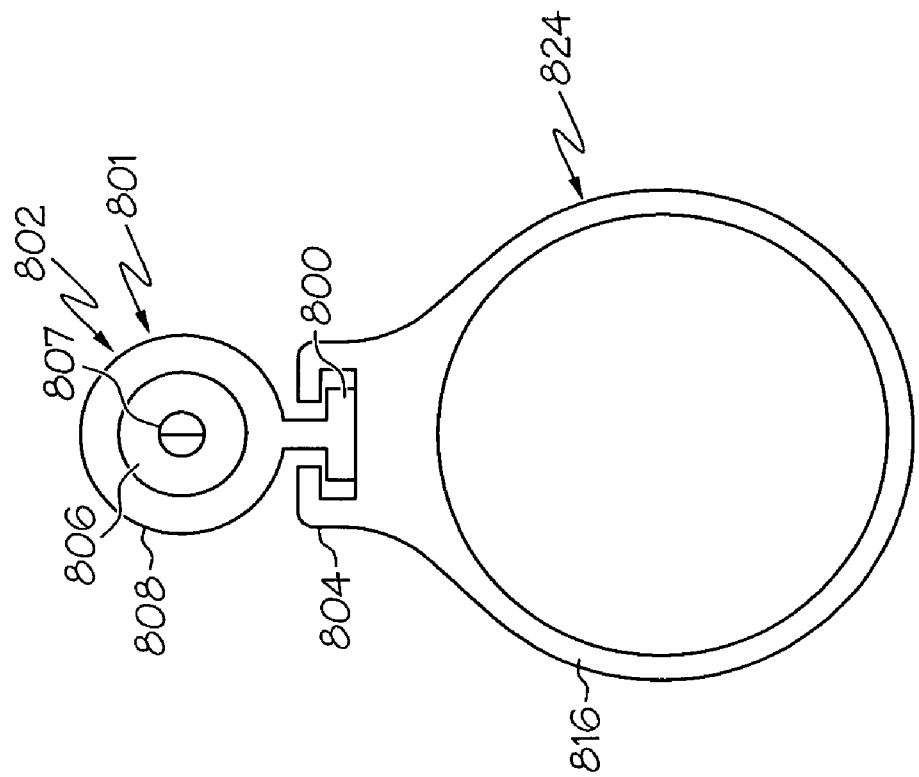
Figure 25:
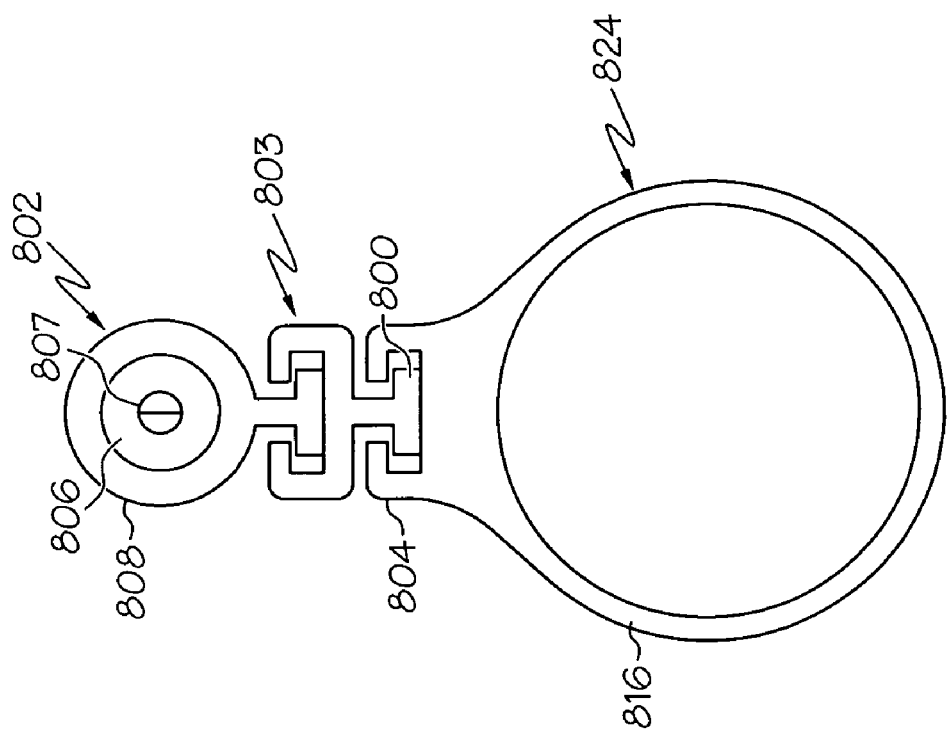
Figure 26:
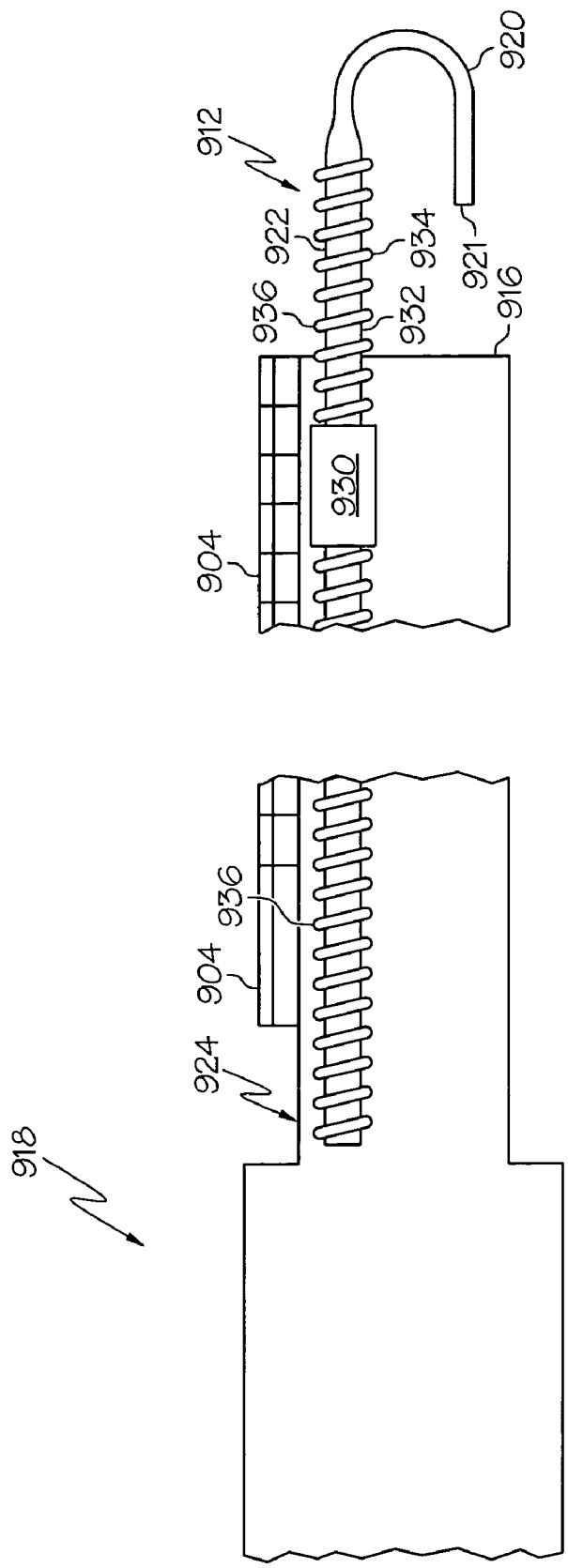
Figure 27:
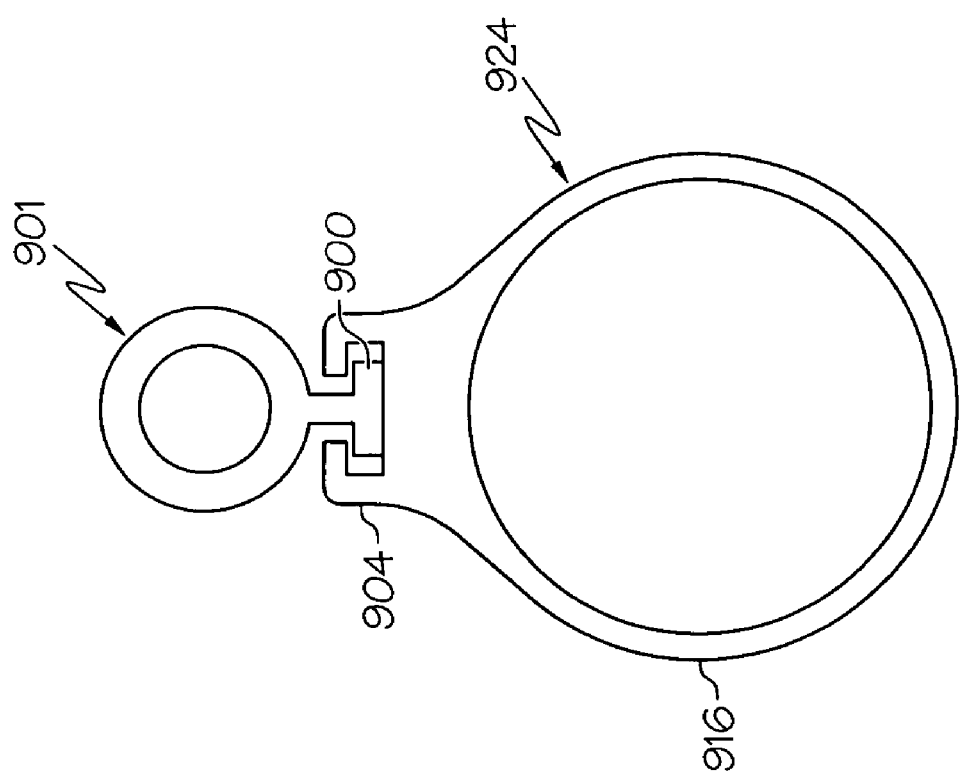

24 is a distal end view of the catheter of FIG. 22 together with an embodiment of an adjunct medical device having a working channel containing a medical device in the form of a cutting blade;

FIG. 25 is a distal end view of the catheter of FIG. 22 together with an embodiment of an adjunct medical device in the form of a connector, wherein the connector is coupled to, and slides along, the rail and wherein the connector is itself adapted to slidably receive a rail-coupling portion of a second medical instrument in the form of the adjunct medical device of FIG. 24;

FIG. 26 is a schematic side-elevational cutaway view of an eighth embodiment of a medical instrument of the invention including a non-loop-track guidewire and an add-to catheter having a rail;

FIG. 27 is a distal end view of the catheter of FIG. 26, with the guidewire and the guidewire passageway opening(s) omitted for clarity, together with an embodiment of an adjunct medical device.

DETAILED DESCRIPTION

Before explaining the several embodiments of the present invention in detail, it should be noted that each embodiment is not limited in its application or use to the details of construction and arrangement of parts and steps illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is further understood that any one or more of the following-described expressions, embodiments, examples, etc. can be combined with any one or more of the other following-described expressions, embodiments, examples, etc.

Guidewire Structure

Figure 1:
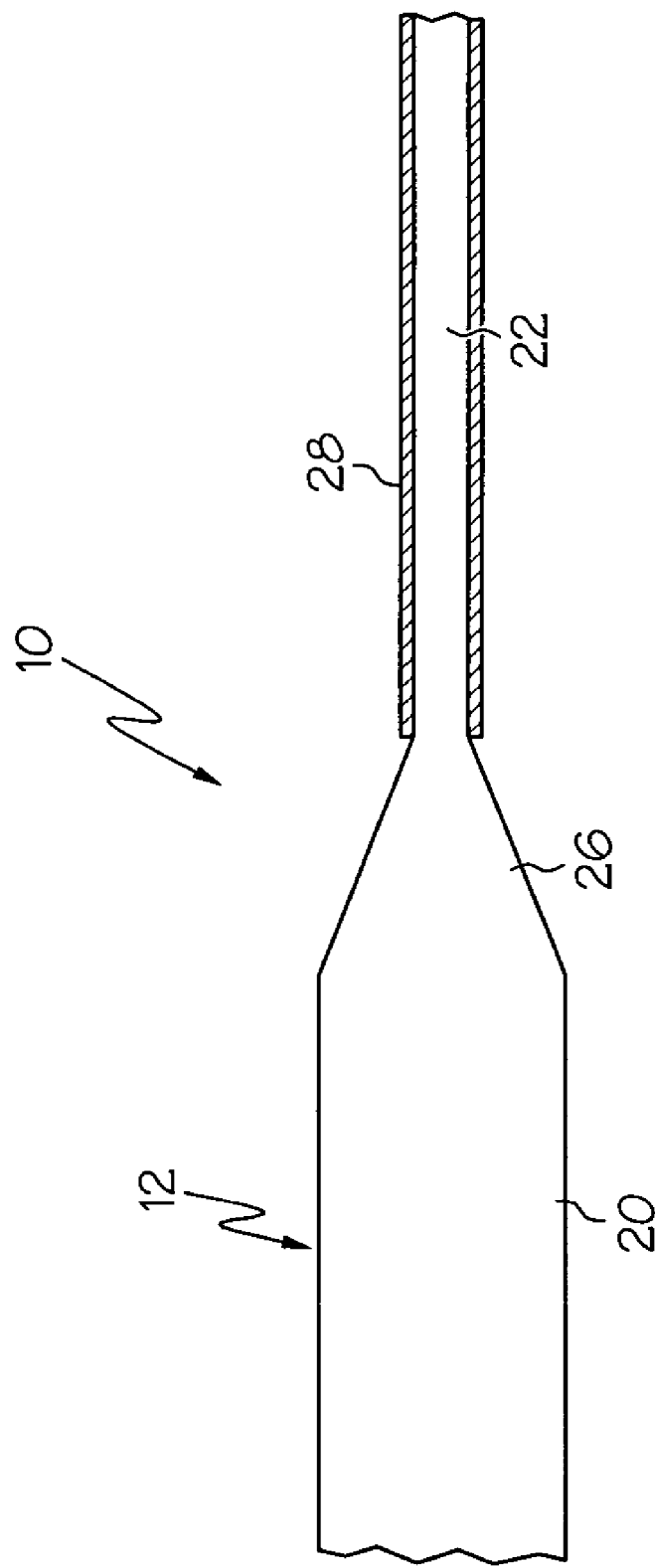
FIG. 1 is a side elevational view of a portion of a first embodiment of a guidewire structure of the invention including a lubricious sleeve shown in cross section.

A first aspect of the invention is directed to a guidewire structure. A first embodiment of a guidewire structure 10 of the invention is shown in FIGS. 1-2 and includes a medical guidewire 12. The medical guidewire 12 includes a working portion 14 which is extendable as a loop track beyond a distal end 16 of a medical instrument 18. The working portion 14 has a maximum loop-track length and includes first and second segments 20 and 22 together having a length greater than ninety percent of the maximum loop-track length. The first segment 20 has a first bending moment of inertia and the second segment 22 has a second bending moment of inertia. The first bending moment of inertia is less than the second bending moment of inertia. It is noted that describing the first bending moment of inertia as less than the second bending moment of inertia is equivalent to describing the first segment 20 as being more flexible than the second segment 22.

It is noted that the term "segments" means non-overlapping segments. It is also noted that the length of the loop track is the distance along the loop track from where the first segment 20 begins to extend beyond the distal end 16 of the medical instrument 18 to where the second segment 22 begins to extend beyond the distal end 16 of the medical instrument 18. It is further noted that when the working portion 14 is not fully extended as a loop track beyond the distal end 16 of the medical instrument 18, the length of the loop track extending beyond the distal end 16 of the medical instrument 18 is less than the maximum loop-track length.

The medical guidewire 12 is adapted to guide the medical instrument 18. In one variation, the medical guidewire 12 is adapted to guide a flexible catheter (also known as a flexible insertion tube) 24 of the medical instrument 18. In one modification, the first and/or second segments 20 and/or 22 are disposed to extend beyond the distal end 16 of the catheter 24 from passageways inside the catheter 24. In one illustration, not shown, the first and second segments 20 and 22 extend from the same passageway. In a different modification, not shown, the first and/or second segments are disposed to extend beyond the distal end of the catheter from outside the exterior surface of the catheter with the second or both of the segments engaged by guide ways on the exterior surface of the catheter. Other modifications are left to the artisan. Examples of catheters include, without limitation, cardiovascular catheters, pulmonary catheters, and insertion tubes of endoscopes such as insertion tubes of gastroscopes and colonoscopes. In one enablement of the embodiment of FIGS. 1-2, the working portion 14 is adapted for patient intraluminal contact. Examples of body lumens of a patient include, without limitation, the upper GI (gastrointestinal) tract, the lower GI tract, and blood vessel passageways. Other examples of medical instruments 18, catheters 24, and/or body lumens are left to the artisan.

In one construction of the guidewire embodiment of FIGS. 1-2, the first segment 20 and the second segment 22 have substantially the same material composition, wherein the first segment 20 has a substantially-constant first diameter, wherein the second segment 22 has a substantially-constant second diameter, and wherein the first diameter is less than the second diameter. In one variation, the working portion 14 includes a third segment 26 extending from the second segment 22 to the first segment 20. The third segment 26 has a length and has a varying third diameter which is substantially equal to the second diameter proximate the second segment 22 and which is substantially equal to the first diameter proximate the first segment 20. In one modification, the varying third diameter of the third segment 26 substantially linearly decreases from proximate the second segment 22 to proximate the first segment 20. In a different modification, the third diameter of the third segment 26 is less than the first and second diameters except proximate the first and second segments 20 and 22.

In one employment of the guidewire embodiment of FIGS. 1-2, the working portion 14 includes a lubricious sleeve 28 surrounding the first segment 20. The sleeve 16 creates a low friction surface for easy passage through a body lumen of a (human or non-human) patient. Examples of materials for the sleeve 28 include, without limitation, Polytetrafluoroethylene (PTFE), such as Striped Teflon® PTFE available from Zeus, Inc (Orangeburg, S.C.). In one method, the sleeve 28 is applied over the first segment 20 through a heat-shrink process well known in the art. In one variation, the working portion 14, apart from the sleeve 28 (or apart from any sleeve), is monolithic.

In one illustration of the guidewire embodiment of FIGS. 1-2, the working portion 14, apart from any sleeve, is made of a super-elastic alloy such as nitinol available from Nitinol Devices & Components (Fremont, Calif.) and has a suitable diameter for insertion into a body lumen of a patient. In one example, the first segment 20 has a length of over 1 meter and a diameter of substantially 0.46 millimeter, the second segment 22 has a length of over 1 meter and a diameter of substantially 0.76 millimeter, the third segment 26 has a length of substantially 0.08 meter, and the sleeve 28 has a wall thickness of substantially 0.11 millimeter. Other dimensional choices are left to the artisan.

One technique for using the guidewire structure 10 of the guidewire embodiment of FIGS. 1-2 includes inserting the first segment 20 into a first guidewire passageway of the catheter 24 from the distal end 16 and inserting the second segment 22 into a second guidewire passageway of the catheter 24 from the distal end 16. Then, with the working portion 14 extended a minimum distance beyond the distal end 16 of the catheter 24, the catheter 24 is manually inserted an initial distance into a body lumen of a patient. Then, a first guidewire leg 12' leading to the first segment 20 is manually pushed from outside the patient to extend at least some of the first segment 20 beyond the distal end 16 of the catheter 24. Then, a second guidewire leg 12" leading to the second segment 22 is pushed from outside the patient to extend at least some of the second segment 22 beyond the distal end 16 of the catheter 24 and to temporarily anchor the second segment 22 against the wall of the body lumen. Then, the first segment 20 is immobilized with respect to the catheter 24 (by the clinician or by the use of a surgical clamp, spring clamp, or collet) and the catheter 24 is manually pushed a further distance into the body lumen while manually pulling on the second guidewire leg 12" from outside the patient to retract at least some of the second segment 22. The last two steps (described in the previous two sentences) are repeated as necessary to fully insert the catheter 24 into the body lumen.

In one example, not shown, of the guidewire embodiment of FIGS. 1-2, the medical guidewire includes surface elevation features to improve the temporary anchoring of the medical guidewire against the wall of the body lumen. In one variation, the surface elevation features are present on then second segment and are absent from the first segment. In the same or a different variation, the surface elevation features are external threads.

Figure 3:
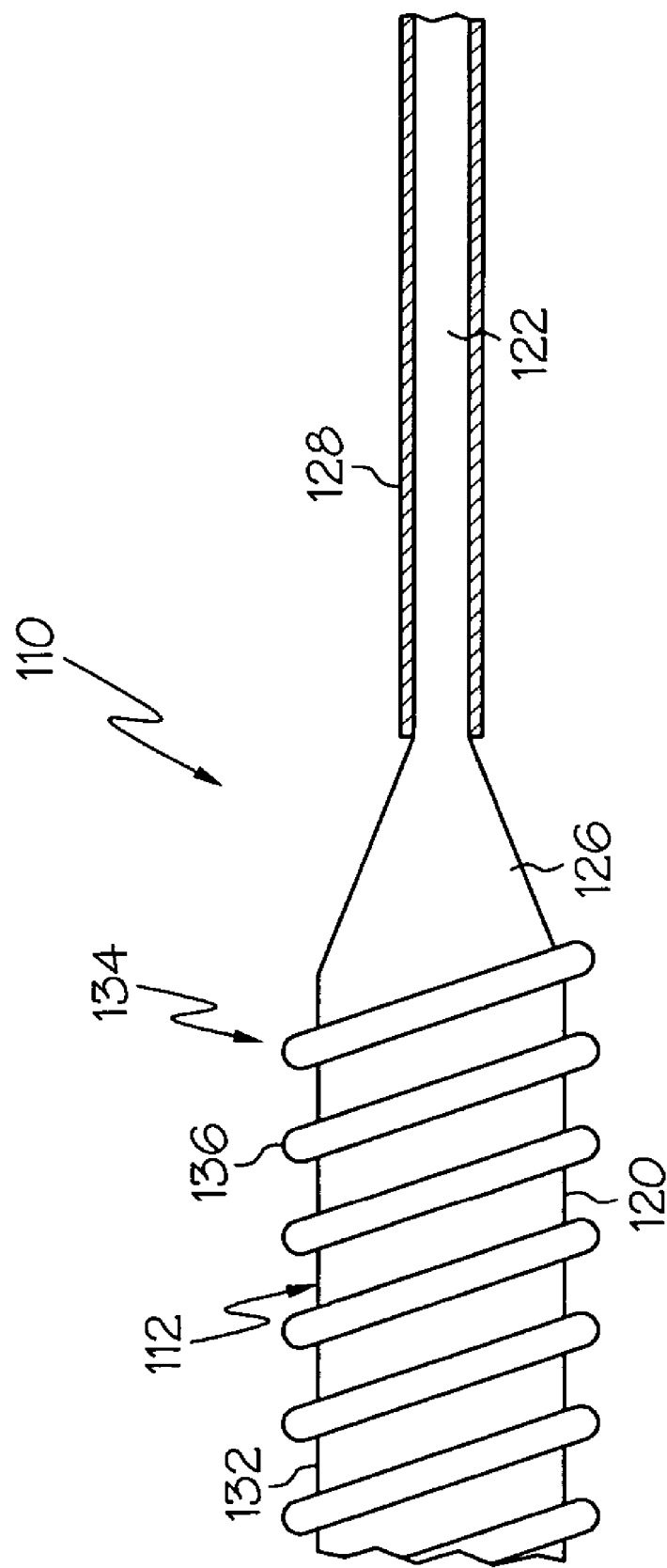
FIG. 3 is a side elevational view of a portion of a second embodiment of a guidewire structure of the invention including external threads and including a lubricious sleeve shown in cross section.
Figure 5:
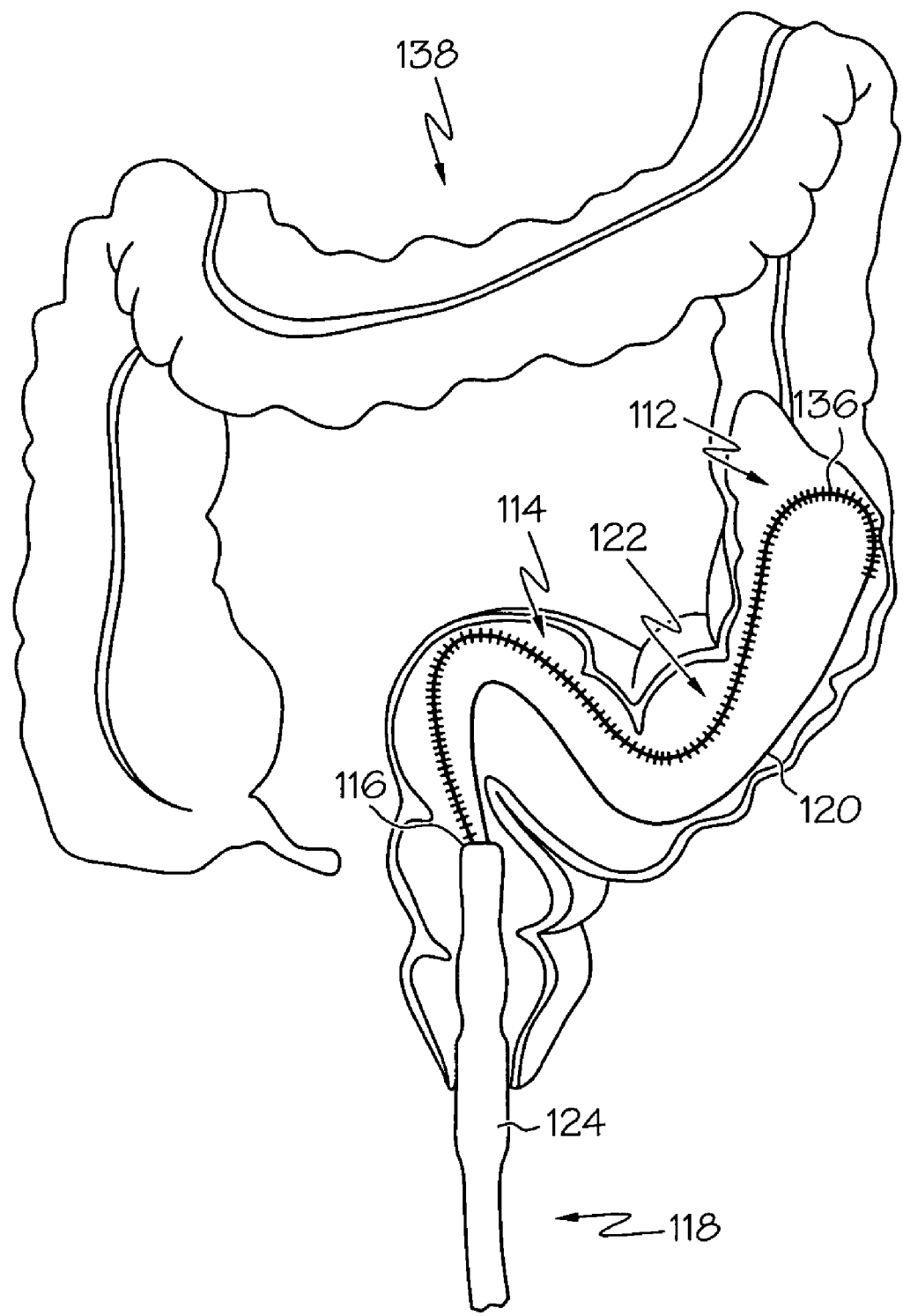
FIG. 5 is a schematic view of a distal end portion of the assemblage of FIG. 4 in the form of an insertion tube of a colonoscope and employed during a colonoscopy.

A second embodiment of a guidewire structure 110 of the invention is shown in FIGS. 3-5. A first expression of the guidewire embodiment of FIGS. 3-5 is for a guidewire structure 110 including a medical guidewire 112. The medical guidewire 112 includes a working portion 114 which is extendable as a loop track beyond a distal end 116 of a medical instrument 118 having a mechanized guidewire drive assembly 130. The working portion 114 includes an exterior surface 132 having a repetitive series of spaced-apart surface elevation features 134 adapted for operable engagement with the mechanized guidewire drive assembly 130.

In one arrangement of the first expression of the guidewire embodiment of FIGS. 3-5, the working portion 114 includes first and second segments 120 and 122, and the surface elevation features 134 are present on the second segment 122 and are absent from the first segment 120. In one variation, the surface elevation features 134 are chosen from the group consisting of periodic threads (also called external threads 136), periodic teeth, periodic holes, and periodic grooves. In the same or a different arrangement, the working portion 114 has a maximum loop-track length, wherein the first and second segments 120 and 122 together have a length greater than ninety percent of the maximum loop-track length, wherein the first segment 120 has a first bending moment of inertia and the second segment 122 has a second bending moment of inertia, and wherein the first bending moment of inertia is less than the second bending moment of inertia.

A second expression of the guidewire embodiment of FIGS. 3-5 is for a guidewire structure 110 including a medical guidewire 112. The medical guidewire 112 includes a working portion 114 which is extendable as a loop track beyond a distal end 116 of a medical instrument 118 having a mechanized guidewire drive assembly 130. The working portion 114 includes an exterior surface 132 having external threads 136 adapted for operable engagement with the mechanized guidewire drive assembly 130.

It is noted that the arrangements previously described for the first expression of the guidewire embodiment of FIGS. 3-5 are equally applicable to the second expression of the guidewire embodiment of FIGS. 3-5 with external threads 136 being the surface elevation feature 134. In one enablement of the second expression of the guidewire embodiment of FIGS. 3-5, the working portion 114 is adapted for patient intraluminal contact. In one example, the medical instrument 118 is a colonoscope which includes a flexible insertion tube (also known as a flexible catheter) 124, and the distal end 116 of the medical instrument 118 is the distal end of the flexible insertion tube 124 of the colonoscope. FIG. 5 shows the working portion 114 of the medical guidewire 112 disposed in the colon 138 of a patient during a colonoscopy. In one variation, not shown in FIGS. 3-5, the insertion tube 124 includes an imager, a light pathway, and at least one medical-device passageway (i.e., working channel) for inserting a medical device, such as a wire snare to biopsy a polyp during a colonoscopy.

In one employment of the second expression of the guidewire embodiment of FIGS. 3-5, the working portion 114 includes a lubricious sleeve 128 surrounding only the first segment 120. In one variation, the working portion 114, apart from the sleeve 128, consists essentially of a nickel-titanium alloy. In one application, the nickel-titanium alloy is nitinol.

In one construction of the second expression of the guidewire embodiment of FIG. 3-5, the first segment 120 and the second segment 122 have substantially the same material composition, wherein the first segment 120 has a substantially-constant first diameter, wherein the second segment 122, without considering the external threads 136, has a substantially-constant second diameter, and wherein the first diameter is less than the second diameter. In one variation, the working portion 114 includes a third segment 126 extending from the second segment 122 to the first segment 120, wherein the third segment 126 has a length and has a varying third diameter which is substantially equal to the second diameter proximate the second segment 122 and which is substantially equal to the first diameter proximate the first segment 120. In one modification, the third diameter of the third segment 126 substantially linearly decreases from proximate the second segment 122 to proximate the first segment. In a different modification, the third diameter of the third segment 126 is less than the first and second diameters except proximate the first and second segments 120 and 122.

A first method for making the guidewire structure 110 of the second expression of the guidewire embodiment of FIGS. 3-5 includes steps a) through e). Step a) includes obtaining a monolithic core wire having a diameter. Step b) includes machining the core wire to create a first section, a second section, and a transition section extending from the second section to the first section, wherein the first and second sections each have a substantially constant diameter, and wherein the first diameter is less than the second diameter. Step c) includes obtaining a helical spring. Step d) includes disposing the helical spring to surround the second section. Step e) includes metallurgically attaching the helical spring to the second section, wherein the first section substantially defines the first segment 120 apart from any sleeve 128, and wherein the second section with the metallurgically-attached helical spring substantially defines the second segment 122.

In one enablement of the first method, step e) is chosen from the group consisting of soldering and laser welding. In the first method, the metallurgically-attached helical spring defines the external threads 136. In the same or a different enablement, the helical spring is a nitinol helical spring having a diameter of between 0.13 millimeter and 0.51 millimeter (and in one construction substantially 0.30 millimeter). In one variation, the external threads 136 have a constant spacing of 40 threads per inch, determining a 0.025 inch pitch, for a fine-pitch application or have a constant spacing of 10 threads per inch, determining a 0.10 inch pitch, for a coarse-pitch application. In another variation, the external threads 136 have a spacing which varies over the length of the second segment 122.

A second method for making the guidewire structure 110 of the second expression of the guidewire embodiment of FIGS. 3-5 includes steps a) and b). Step a) includes obtaining a monolithic core wire. Step b) includes machining the core wire to create the first segment 120, apart from any sleeve 128, and to create the second segment 122 including the external threads 136.

One technique for using the guidewire structure 110 of the second expression of the guidewire embodiment of FIGS. 3-5 includes inserting the first segment 120 into a first guidewire passageway of the catheter 124 from the distal end 116 and inserting the second segment 122 into a second guidewire passageway of the catheter 124 from the distal end 116 to engage the mechanized guidewire drive assembly 130. Then, with the working portion 114 extended a minimum distance beyond the distal end 116 of the catheter 124, the catheter 124 is manually inserted an initial distance into a body lumen of a patient. Then, a first guidewire leg 112' leading to the first segment 120 is manually pushed from outside the patient to extend at least some of the first segment 120 beyond the distal end 116 of the catheter 124. Then, the mechanized guidewire drive assembly 130 is used to push the second segment 122 to extend at least some of the second segment 122 beyond the distal end 116 of the catheter 124 and to temporarily anchor the second segment 122 against the wall of the body lumen. Then, the catheter 124 is manually pushed a further distance into the body lumen while the mechanized guidewire drive assembly 130 is used to pull on the second segment 122 to retract at least some of the second segment 122 into the catheter 124. The last two steps are repeated as necessary to fully insert the catheter 124 into the body lumen.

Figure 6:
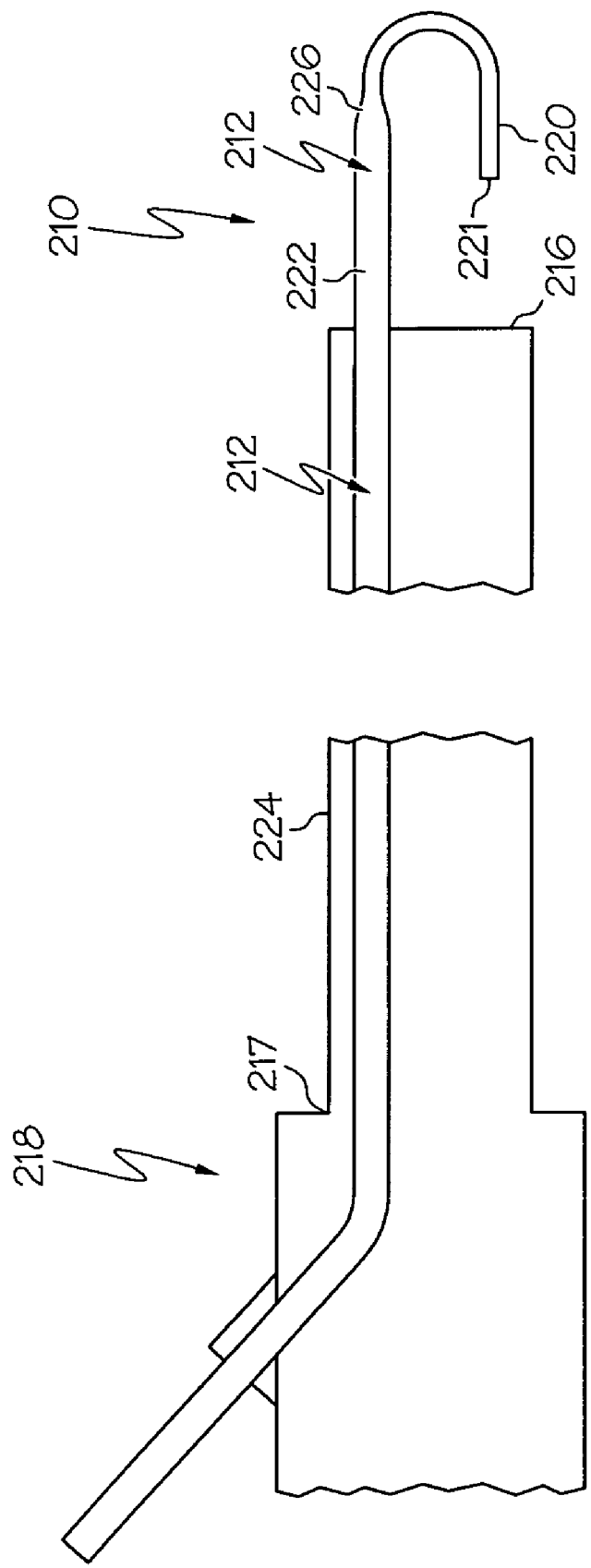
FIG. 6 is a schematic side-elevational cutaway view of a portion of an alternate first embodiment of a guidewire structure, with the sleeve omitted for clarity, employed in an alternate first embodiment of a medical instrument having a catheter.

An alternate first embodiment of a guidewire structure 210 is shown in FIG. 6 and includes a medical guidewire 212. The medical guidewire 212 is extendable beyond a distal end 216 of a medical instrument 218. The medical guidewire 212 includes first and second segments 220 and 222, wherein the first segment 220 has a first bending moment of inertia and the second segment 222 has a second bending moment of inertia, and wherein the first bending moment of inertia is less than the second bending moment of inertia. The first segment 220 has a free end 221 which extends beyond the distal end 216 of the medical instrument 218 when the medical guidewire 212 is fully extended. It is noted that such fee end 221 makes the medical guidewire 212 a non-loop-track medical guidewire.

In one application of the guidewire structure 210 of FIG. 6, the anchoring generally comes from the first segment 220 folding back and having the second segment 222 begin to fold back. In one variation, the portion of the medical guidewire 212 which can extend beyond the distal end 216 of the catheter 224 has a long length. In one example, the first segment 220 has a length between 50 millimeters and 1 meter and has a diameter of substantially 0.25 millimeter, the second segment 222 has a length over 1 meter and has a diameter of substantially 0.76 millimeter, and the third segment 226 has a length of substantially 0.08 meter.

One technique for using the guidewire structure 210 of FIG. 6 includes inserting the first guidewire segment 220 into a guidewire passageway of the catheter 224 from the proximal end 217. Further advancement of the guidewire structure 210 will result in advancement of the second guidewire segment 222 into the same guidewire passageway from the proximal end 217. The catheter 224 is manually inserted into a body lumen of a patient. Then, the second guidewire portion 222 is manually advanced from the proximal end 217 outside the patient to extend the first segment 220 and at least a portion of the second segment 222 beyond the distal end 216 of the catheter 224 to temporarily anchor the second segment 222 against the wall of the body lumen. Then, the catheter 224 is manually pushed a further distance into the body lumen while manually pulling on the second segment 222 from outside the patient. The last two steps are repeated as necessary to fully insert the catheter 224 into the body lumen.

An alternate second embodiment of a guidewire structure is shown in FIG. 7. A first expression of the guidewire structure 310 of FIG. 7 includes a medical guidewire 312 which is extendable beyond a distal end 316 of a medical instrument 318 having a mechanized guidewire drive assembly 330. The medical guidewire 312 includes an exterior surface 332 having a repetitive series of spaced-apart surface elevation features 334 adapted for operable engagement with the mechanized guidewire drive assembly 330. The medical guidewire 312 has a free end 321 which extends beyond the distal end 316 of the medical instrument 318 when the medical guidewire 312 is fully extended. It is noted that such fee end 321 makes the medical guidewire 312 a non-loop-track medical guidewire.

A second expression of the guidewire structure 310 of FIG. 7 includes a medical guidewire 312 which is extendable beyond a distal end 316 of a medical instrument 318 having a mechanized guidewire drive assembly 330. The medical guidewire 312 includes an exterior surface 332 having external threads 336 adapted for operable engagement with the mechanized guidewire drive assembly 330. The medical guidewire 312 has a free end 321 which extends beyond the distal end 316 of the medical instrument 318 when the medical guidewire 312 is fully extended.

In one application of the second expression of the guidewire structure 310 of FIG. 7, the external threads 336 themselves act to anchor the medical guidewire 312 when the external threads 336 are disposed along the wall of the body lumen, independent of any medical-guidewire fold back and especially when the external threads 336 extend far into the body lumen from the distal end 316 of the medical instrument 318. In one example, the first segment 320 has a length between 50 millimeters and 1 meter and has a diameter of substantially 0.25 millimeter, the second segment 322 has a length over 1 meter and has a diameter of substantially 0.76 millimeter, and the third segment 326 has a length of substantially 0.08 meter.

One technique for using the second expression of the guidewire structure 310 of FIG. 7 includes inserting the second segment 322 into a guidewire passageway of catheter 324 from the distal end 316 to engage a mechanized guidewire assembly 330. In one variation, the mechanized drive assembly 330 is used to draw all of the guidewire structure 310, including second segment 322 and first segment 320, within the catheter 324. A second guidewire passageway, if present, of the catheter 324 is left completely open for other accessories. Then, the mechanized guidewire assembly 330 is used to push the first segment 320 and a portion of the second segment 322 to extend beyond the distal end 316 of the catheter 324 into the body lumen and to temporarily anchor the second segment 322 against the wall of the body lumen. Then, the catheter 324 is manually pushed a further distance into the body lumen while the mechanized guidewire drive assembly 330 is used to pull on the second segment 322 to retract at least some of second segment 322 into the catheter 324. The last two steps are repeated as necessary to fully insert the catheter 324 into the body lumen.

Medical Instrument Having a Medical Guidewire

A second aspect of the invention is directed to a medical instrument having a medical guidewire. A first embodiment of a medical instrument 18 of the invention is shown in FIGS. 1-2 and includes a flexible catheter 24 and a medical guidewire 12. The catheter 24 has a distal end 16 insertable into a body lumen of a patient. The medical guidewire 12 includes a working portion 14 which is extendable as a loop track beyond the distal end 16 of the catheter 24. The working portion 14 has a maximum loop-track length and includes first and second segments 20 and 22 together having a length greater than ninety percent of the maximum loop-track length. The first segment 20 has a first bending moment of inertia and the second segment 22 has a second bending moment of inertia. The first bending moment of inertia is less than the second bending moment of inertia. In one example, the catheter 24 is an insertion tube of a flexible endoscope (with the endoscope imager, working channel, etc. omitted from FIGS. 1-2 for clarity).

A method for operating the medical instrument 18 of the medical-instrument embodiment of FIGS. 1-2 is now described, wherein the medical guidewire 12 includes a first guidewire leg 12' having a free end disposed outside the patient and leading to the first segment 20 and includes a second guidewire leg 12" having a free end disposed outside the patient and leading to the second segment 22. The method includes steps a) through d). Step a) includes manually inserting the distal end 16 of the catheter 24 an initial distance into the body lumen of the patient. Step b) includes manually pushing the first guidewire leg 12' to extend at least some of the first segment 20 beyond the distal end 16 of the catheter 24. Step c) includes manually pushing the second guidewire leg 12" to extend at least some of the second segment 22 beyond the distal end 16 of the catheter 24 and to temporarily anchor the second segment 22 against a wall of the body lumen. Step d) includes immobilizing the first guidewire leg 12' with respect to the catheter 24 and manually pushing the catheter 24 a further distance into the body lumen while manually pulling on the second guidewire leg 12" to retract at least some of the second segment 22. In one extension of the method, steps c) and d) are repeated.

A second embodiment of a medical instrument 118 of the invention is shown in FIGS. 3-5 and 8-11. A first expression of the medical-instrument embodiment of FIGS. 3-5 and 8-11 is for a medical instrument 118 including a flexible catheter 124, a mechanized guidewire drive assembly 130, and a medical guidewire 112. The catheter 124 has a distal end 116 insertable into a body lumen of a patient. The medical guidewire 112 includes a working portion 114 which is extendable as a loop track beyond the distal end 116 of the catheter 124. The working portion 114 includes an exterior surface 132 having a repetitive series of spaced-apart surface elevation features 134 adapted for operable engagement with the mechanized guidewire drive assembly 130.

In one arrangement of the first expression of the medical-instrument embodiment of FIGS. 3-5 and 8-11, the mechanized guidewire drive assembly 130 includes a surface-elevation-feature engaging component 140 disposed within the catheter 124 toward the distal end 116 of the catheter 124. "Toward the distal end" means closer to the distal end than to the proximal end. Examples of surface-elevation-feature engaging components include, without limitation, a nut gear 142, a worm gear, a spoke gear, etc. It is noted that the previously-described arrangements, variations, etc. of the first expression of the guidewire embodiment of FIGS. 3-5 are equally applicable to the first expression of the medical-instrument embodiment of FIGS. 3-5 and 8-11.

A second expression of the medical-instrument embodiment of FIGS. 3-5 and 8-11 is for a medical instrument 118 including a flexible catheter 124, a mechanized guidewire drive assembly 130, and a medical guidewire 112. The catheter 124 has a distal end 116 insertable into a body lumen of a patient. The medical guidewire 112 includes a working portion 114 which is extendable as a loop track beyond the distal end 116 of the catheter 124. The working portion 114 includes an exterior surface 132 having external threads 136 adapted for operable engagement with the mechanized guidewire drive assembly 130.

In a first construction of the second expression of the medical-instrument embodiment of FIGS. 3-5 and 8-11, the mechanized guidewire drive assembly 130 includes a motor 144, a spur gear 146, and a nut gear 142. The motor 144 has a rotatable motor shaft 148, and the spur gear 146 is attached to the motor shaft 148. The nut gear 142 includes external teeth 150 which are engaged by the spur gear 146. The nut gear 142 includes internal threads 152 which threadably engage the external threads 136 of the medical guidewire 112. The spur gear 146 and the nut gear 142 are disposed within the catheter 124.

In one variation of the first construction, the motor 144 is disposed within the catheter 124. In a different variation, not shown, the motor is disposed outside the proximal end of the catheter, wherein the motor shaft of the motor is a flexible motor shaft. In one modification, not shown, the motor is disposed in the handle of the medical instrument. In another modification, not shown, the motor is disposed in a console. Other motor locations are left to the artisan. In one application, the motor 144 is a rotary motor. In a different application, the mechanized guidewire drive assembly includes a linear motor.

In a second construction (not shown) of the second expression of the medical-instrument embodiment of FIGS. 3-5 and 8-11, the mechanized guidewire drive assembly 130 does not include a motor but does include a non-motorized mechanism which the clinician uses to extend the medical guidewire. In one example, the non-motorized mechanism includes a hand crank which has a rotatable flexible output shaft leading to a gearbox operatively connectable to the medical guidewire. Other examples are left to the artisan.

In one enablement of the second expression of the medical-instrument embodiment of FIGS. 3-5 and 8-11, the working portion 114 includes first and second segments 120 and 122. The external threads 136 are present on the second segment 122 and are absent from the first segment 120. In one variation, the working portion 114 has a maximum loop-track length, wherein the first and second segments 120 and 122 together have a length greater than ninety percent of the maximum loop-track length. In this variation, the first segment 120 has a first bending moment of inertia and the second segment 122 has a second bending moment of inertia, wherein the first bending moment of inertia is less than the second bending moment of inertia. In one modification, the working portion 114 includes a third segment 126 extending from the second segment 122 to the first segment 120, wherein the third segment 126 has a length and has a varying third diameter. The varying third diameter is substantially equal to the second diameter proximate the second segment 122 and is substantially equal to the first diameter proximate the first segment 120. In one example, the internal threads 152 of the nut gear 142 are disposed a distance from the distal end 116 of the catheter 124 substantially equal to the length of the third segment 126 of the working portion 114 of the medical guidewire 112.

In one deployment of the second expression of the medical-instrument embodiment of FIGS. 3-5 and 8-11, the catheter 124 is an insertion tube of a flexible endoscope (with the endoscope imager, working channel, etc. omitted from FIGS. 3-5 and 8-11 for clarity). In one variation, the working portion 114 includes a lubricious sleeve 128 surrounding only the first segment 120. In one choice of materials, the working portion 114, apart from the sleeve 128, consists essentially of a nickel-titanium alloy. In one application, the nickel-titanium alloy is nitinol.

This paragraph describes in more detail one configuration of an embodiment of the mechanized guidewire drive assembly 130. As shown in FIG. 8, the first segment 120 of the medical guidewire 112 is seen extending from the first guidewire passageway 154 within the catheter 124, and the second segment 122 of the medical guidewire 112 is seen extending from the second guidewire passageway 156 within the catheter 124. In this configuration, the catheter 124 includes a more rigid portion 158 (such as an injection molded polycarbonate or other plastic portion having two halves which fit together in a clamshell fashion) which houses the mechanized guidewire drive assembly 130 and which has stabilizing ribs 160 to constrain the motor 144. The medical instrument 118 also includes a lead 162 supplying power to the motor 144. In one example, the motor 144 is a miniature DC (direct current) motor such as Faulhaber motor model 0816-006 (available from MicroMo Electronics, Inc. of Clearwater, Fla.) with a gearbox having a reduction ratio of 64:1. In this example, the spur gear 146 has 12 teeth, has a pitch diameter of 8 millimeters, and is supported on its non-motor side by a gear bearing 164. In this example, the nut gear 142 has 6 or 12 external teeth 150 and is linearly constrained by a pair of bosses 166. Thus, rotation and counter-rotation of the motor 144 results in extension and retraction of the second segment 122 of the medical guidewire 112. In one application, air is introduced into the body lumen through the first guidewire passageway 154 during a colonoscopy. In an alternate configuration, not shown, the spur gear is disposed between two universal joints which together are disposed between two smaller motors to provide a tighter bending radius for the catheter, as can be appreciated by those skilled in the art. Other configurations are left to the artisan.

A method for operating the medical instrument 118 of the second expression of the medical-instrument embodiment of FIGS. 3-5 and 8-11 is now described, wherein the medical guidewire 112 includes a first guidewire leg 112' having a free end disposed outside the patient and leading to the first segment 120. The method includes steps a) through d). Step a) includes manually inserting the distal end 116 of the catheter 124 an initial distance into the body lumen of the patient. Step b) includes manually pushing the first guidewire leg 112' to extend at least some of the first segment 120 beyond the distal end 116 of the catheter 124. Step c) includes using the mechanized guidewire drive assembly 130 to extend at least some of the second segment 122 beyond the distal end 116 of the catheter 124 and to temporarily anchor the second segment 122 against a wall of the body lumen. Step d) includes manually pushing the catheter 124 a further distance into the body lumen while using the mechanized guidewire drive assembly 130 to pull on the second segment 122 to retract at least some of the second segment 122 into the catheter 124. In one extension of the method, steps c) and d) are repeated.

An alternate first embodiment of a medical instrument 218 is shown in FIG. 6 and includes a flexible catheter 224 and a medical guidewire 212. The catheter 224 has a distal end 216 insertable into a body lumen of a patient. The medical guidewire 212 is extendable beyond the distal end 216 of the catheter 224. The medical guidewire 212 includes first and second segments 220 and 222, wherein the first segment 220 has a first bending moment of inertia and the second segment 222 has a second bending moment of inertia, and wherein the first bending moment of inertia is less than the second bending moment of inertia. The first segment 220 has a free end 221 which extends beyond the distal end 216 of the catheter 224 when the medical guidewire 212 is fully extended.

An alternate second embodiment of a medical instrument is shown in FIG. 7. A first expression of the medical-instrument 318 of FIG. 7 includes a flexible catheter 324, a mechanized guidewire drive assembly 330, and a medical guidewire 312. The catheter 324 has a distal end 316 insertable into a body lumen of a patient. The medical guidewire 312 is extendable beyond the distal end 316 of the catheter 324. The medical guidewire 312 includes an exterior surface 332 having a repetitive series of spaced-apart surface elevation features 334 adapted for operable engagement with the mechanized guidewire drive assembly 330. The medical guidewire 312 has a free end 321 which extends beyond the distal end 316 of the catheter 324 when the medical guidewire 312 is fully extended.

A second expression of the medical instrument 318 of FIG. 7 includes a flexible catheter 324, a mechanized guidewire drive assembly 330, and a medical guidewire 312. The catheter 324 has a distal end 316 insertable into a body lumen of a patient. The medical guidewire 312 is extendable beyond the distal end 316 of the catheter 324. The medical guidewire 312 includes an exterior surface 332 having external threads 336 adapted for operable engagement with the mechanized guidewire drive assembly 330. The medical guidewire 312 has a free end 321 which extends beyond the distal end 316 of the catheter 324 when the medical guidewire 312 is fully extended.

Medical Instrument Having a Controlled Guidewire Feed

Figure 12:
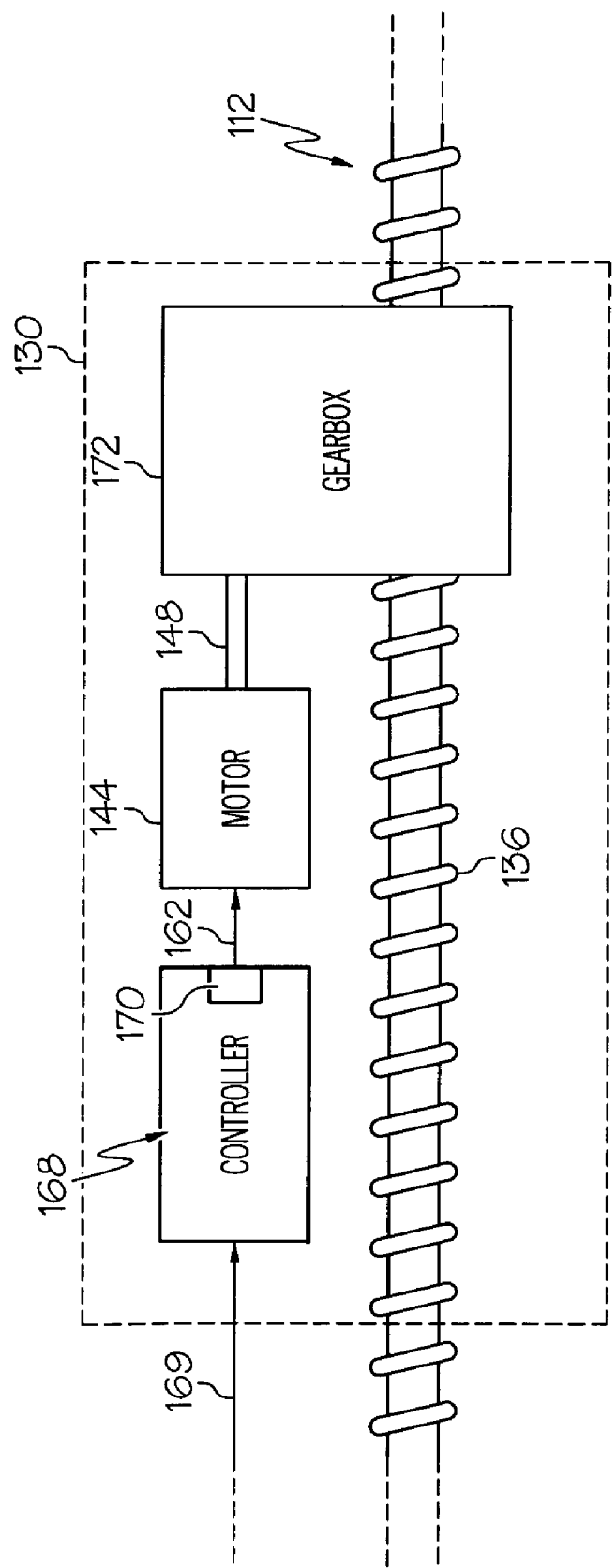
FIG. 12 is a schematic view of another particular embodiment of the mechanized guidewire drive assembly of FIG. 4.

A third aspect of the invention is directed to a medical instrument having a controlled guidewire feed, a first embodiment of which is shown in FIGS. 3-4 and 12. A first expression of the embodiment of FIGS. 3-4 and 12 is for a medical instrument 118 including a flexible catheter 124, a medical guidewire 112, and a mechanized guidewire drive assembly 130. The catheter 124 has a distal end 116 insertable into a body lumen of a patient. The mechanized guidewire drive assembly 130 is adapted for operable engagement with the medical guidewire 112 to extend the medical guidewire 112 beyond the distal end 116 of the catheter 124. The mechanized guidewire drive assembly 130 includes a motor 144 and includes a controller 168 which drives the motor 144 with a driving force, wherein the driving force has a predetermined upper limit.

In the broadest application of the third aspect of the invention, as described in the previous paragraph, the medical guidewire 112 can be a loop-track or a non-loop-track medical guidewire, the medical guidewire 112 may have, but does not require, segments having different bending moment indices and/or different diameters (or other different cross-sectional shapes/sizes), and the medical guidewire 112 may have, but does not require, surface elevation features 134 such as external threads 136. In one illustration, not shown, a mechanized pinch roller extends a smooth-exterior-surfaced medical guidewire beyond the distal end of the catheter.

In one deployment of the first expression of the embodiment of FIGS. 3-4 and 12, the motor 144 is a rotary motor which produces a torque in response to the driving force of the controller 168. In one variation, the motor 144 is a DC (direct current) motor, wherein the driving force is an electric current, wherein the torque is related to the electric current, wherein the predetermined upper limit is a predetermined electric-current upper limit, and wherein the controller 168 includes a current limiter 170 which limits the electric current to the predetermined electric-current upper limit. In one implementation, the predetermined electric-current upper limit is experimentally established from at least measurements of the torque of the DC motor and a comfort level of at least one patient undergoing at least one medical procedure using the medical instrument 118 without any predetermined electric-current upper limit. Other types of driving forces such as, without limitation, pulse-width-modulation (PWM) and other types of motors are left to the artisan. In one example, a lead 169 supplies power to the controller 168 and a lead 162 supplies power to the motor 144 from the controller 168.

In one enablement of the first expression of the embodiment of FIGS. 3-4 and 12, the medical guidewire 112 includes a working portion 114 which is extendable as a loop track beyond the distal end 116 of the catheter 124, wherein the working portion 114 has a maximum loop-track length and includes first and second segments 120 and 122 together having a length greater than ninety percent of the maximum loop-track length. In this enablement, the first segment 120 has a first bending moment of inertia and the second segment 122 has a second bending moment of inertia, wherein the first bending moment of inertia is less than the second bending moment of inertia. In this enablement, the mechanized guidewire drive assembly 130 is adapted for operable engagement with the second segment and not the first segment.

In one construction of the first expression of the embodiment of FIGS. 3-4 and 12, the motor 144 is disposed within substantially fifty centimeters of the distal end 116 of the catheter 124. In one variation, the catheter 124 is an insertion tube of a flexible endoscope. It is noted that in one utilization, having the motor 144 disposed toward, and even proximate, the distal end 116 of the catheter 124 reduces the length of the motor shaft 148 leading to the gearbox 172 which better relates patient discomfort to motor driving force, as can be appreciated by those skilled in the art. In one modification, the gearbox 172 includes the spur gear 146 and nut gear 142 arrangement of the particular embodiment of the mechanized guidewire drive assembly 130 shown in FIG. 8.

A second expression of the embodiment of FIGS. 3-4 and 12 is for a medical instrument 118 including a flexible catheter 124, a medical guidewire 112, and a mechanized guidewire drive assembly 130. The catheter 124 has a distal end 116 insertable into a body lumen of a patient. The medical guidewire 112 includes a working portion 114 which is extendable as a loop track beyond the distal end 116 of the catheter 124, wherein the working portion 114 includes an exterior surface 132 having a repetitive series of spaced-apart surface elevation features 134. The mechanized guidewire drive assembly 130 is adapted for operable engagement with the surface elevation features 134. The mechanized guidewire drive assembly 130 includes a motor 144 and includes a controller 168 which drives the motor 144 with a driving force, wherein the driving force has a predetermined upper limit.

In one employment of the second expression of the embodiment of FIGS. 3-4 and 12, the working portion 114 includes first and second segments 120 and 122, wherein the surface elevation features 134 are present on the second segment 122 and are absent from the first segment 120. It is noted that the deployments, enablements, constructions, etc. of the previously described first expression of the embodiment of FIGS. 3-4 and 12 are equally applicable to the second expression of the embodiment of FIGS. 3-4 and 12.

A third expression of the embodiment of FIGS. 3-4 and 12 is for a medical instrument 118 including a flexible catheter 124, a medical guidewire 112, and a mechanized guidewire drive assembly 130. The catheter 124 has a distal end 116 insertable into a body lumen of a patient. The medical guidewire 112 includes a working portion 114 which is extendable as a loop track beyond the distal end 116 of the catheter 124, wherein the working portion 114 includes an exterior surface 132 having external threads 136. The mechanized guidewire drive assembly 130 is adapted for operable engagement with the external threads 136. The mechanized guidewire drive assembly 130 includes a motor 144 and includes a controller 168 which drives the motor 144 with a driving force, wherein the driving force has a predetermined upper limit.

In one employment of the third expression of the embodiment of FIGS. 3-4 and 12, the working portion 114 includes first and second segments 120 and 122, wherein the external threads 136 are present on the second segment 122 and are absent from the first segment 120. It is noted that the deployments, enablements, constructions, etc. of the previously described first expression of the embodiment of FIGS. 3-4 and 12 are equally applicable to the third expression of the embodiment of FIGS. 3-4 and 12.

Figure 13:
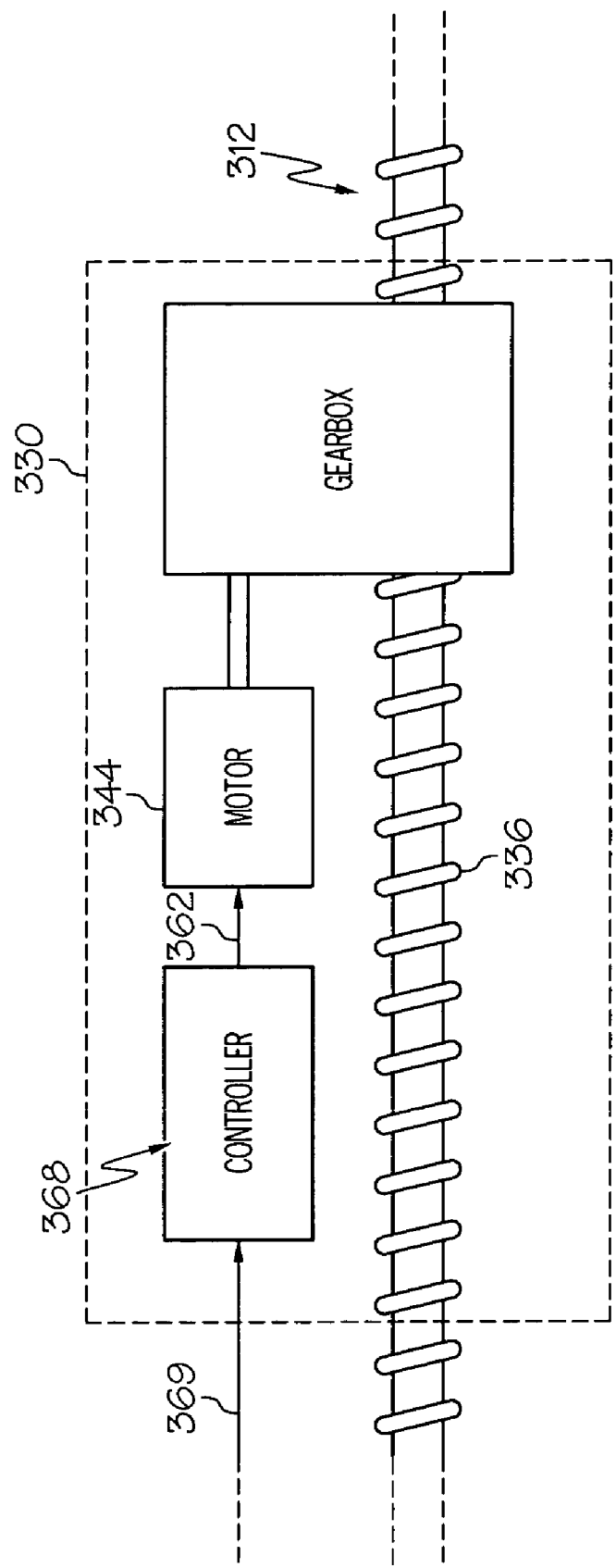
FIG. 13 is a schematic view of a particular embodiment of the mechanized guidewire drive assembly of FIG. 7.

A second embodiment of the third aspect of the invention is shown in FIGS. 7 and 13. A first expression of the embodiment of FIGS. 7 and 13 is for a medical instrument 318 including a flexible catheter 324, a medical guidewire 312, and a mechanized guidewire drive assembly 330. The catheter 324 has a distal end 316 insertable into a body lumen of a patient. The medical guidewire 312 is extendable beyond the distal end 316 of the catheter 324. The medical guidewire 312 includes an exterior surface 332 having a repetitive series of spaced-apart surface elevation features 334. The medical guidewire 312 has a free end 321 which extends beyond the distal end 316 of the catheter 324 when the medical guidewire 312 is fully extended. The mechanized guidewire drive assembly 330 is adapted for operable engagement with the surface elevation features 334. The mechanized guidewire drive assembly 330 includes a motor 344 and includes a controller 368 which drives the motor 344 with a driving force, wherein the driving force has a predetermined upper limit.

A second expression of the embodiment of FIGS. 7 and 13 is for a medical instrument 318 including a flexible catheter 324, a medical guidewire 312, and a mechanized guidewire drive assembly 330. The catheter 324 has a distal end 316 insertable into a body lumen of a patient. The medical guidewire 312 is extendable beyond the distal end 316 of the catheter 324. The medical guidewire 312 includes an exterior surface 332 having external threads 336. The medical guidewire 312 has a free end 321 which extends beyond the distal end 316 of the catheter 324 when the medical guidewire 312 is fully extended. The mechanized guidewire drive assembly 330 is adapted for operable engagement with the external threads 336. The mechanized guidewire drive assembly 330 includes a motor 344 and includes a controller 368 which drives the motor 344 with a driving force, wherein the driving force has a predetermined upper limit.

In one example of the second expression of the embodiment of FIGS. 7 and 13, a lead 369 supplies power to the controller 368 and a lead 362 supplies power to the motor 344 from the controller 368.

Medical Instrument Having a Catheter and a Medical Guidewire

Figure 14:
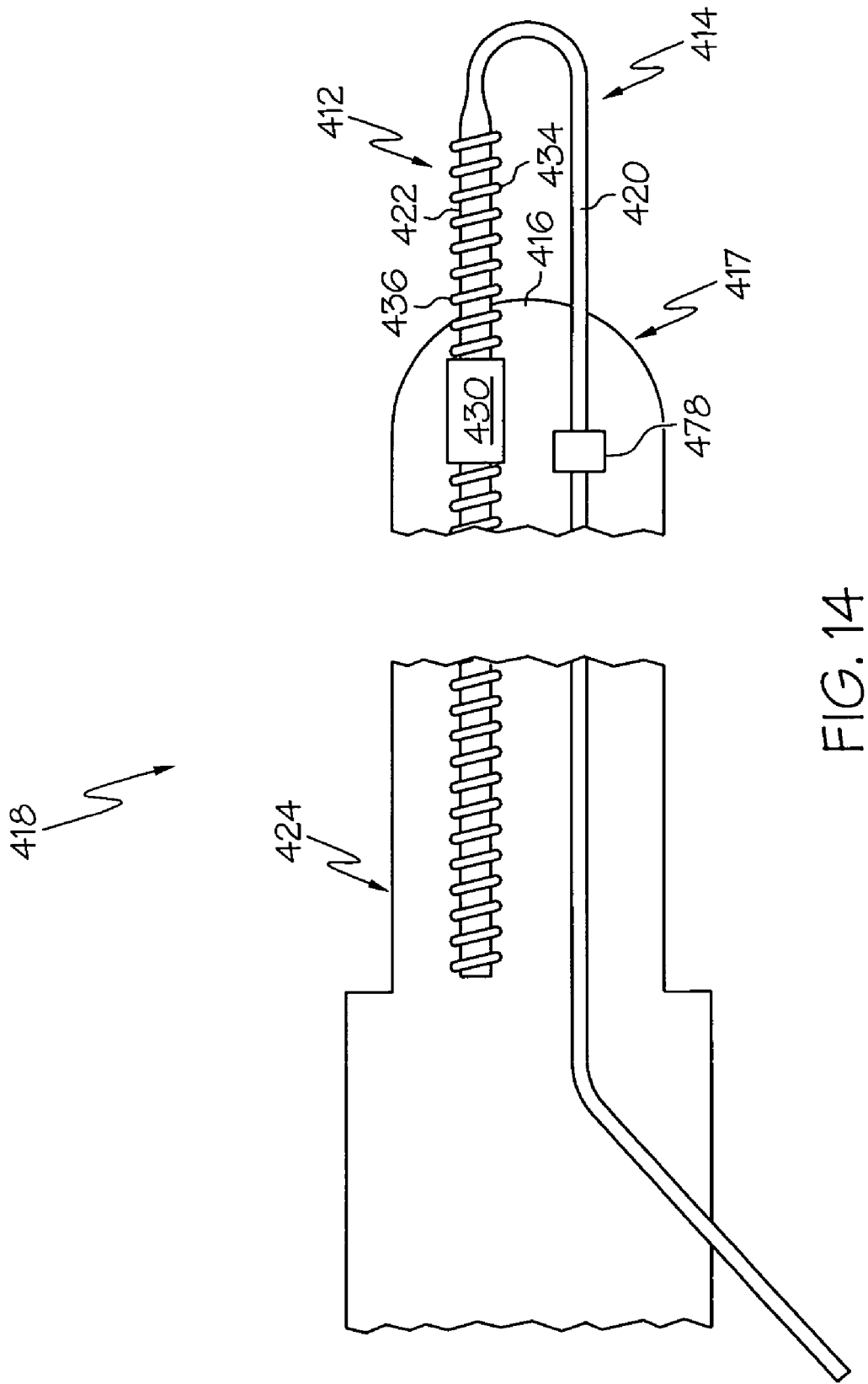
FIG. 14 is a schematic side-elevational cutaway view of a portion of a third embodiment of a medical instrument of the invention including a catheter and a medical guidewire.
Figure 15:
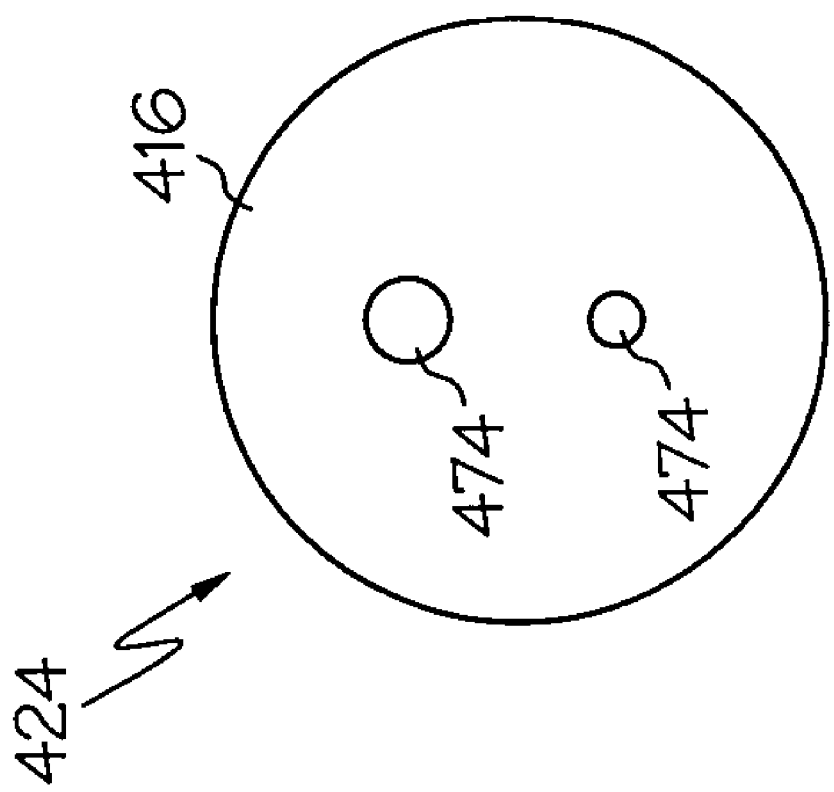
FIG. 15 is a front elevational view of the catheter of the medical instrument of FIG. 14 with the medical guidewire removed to show two guidewire passageway openings.
Figure 16:
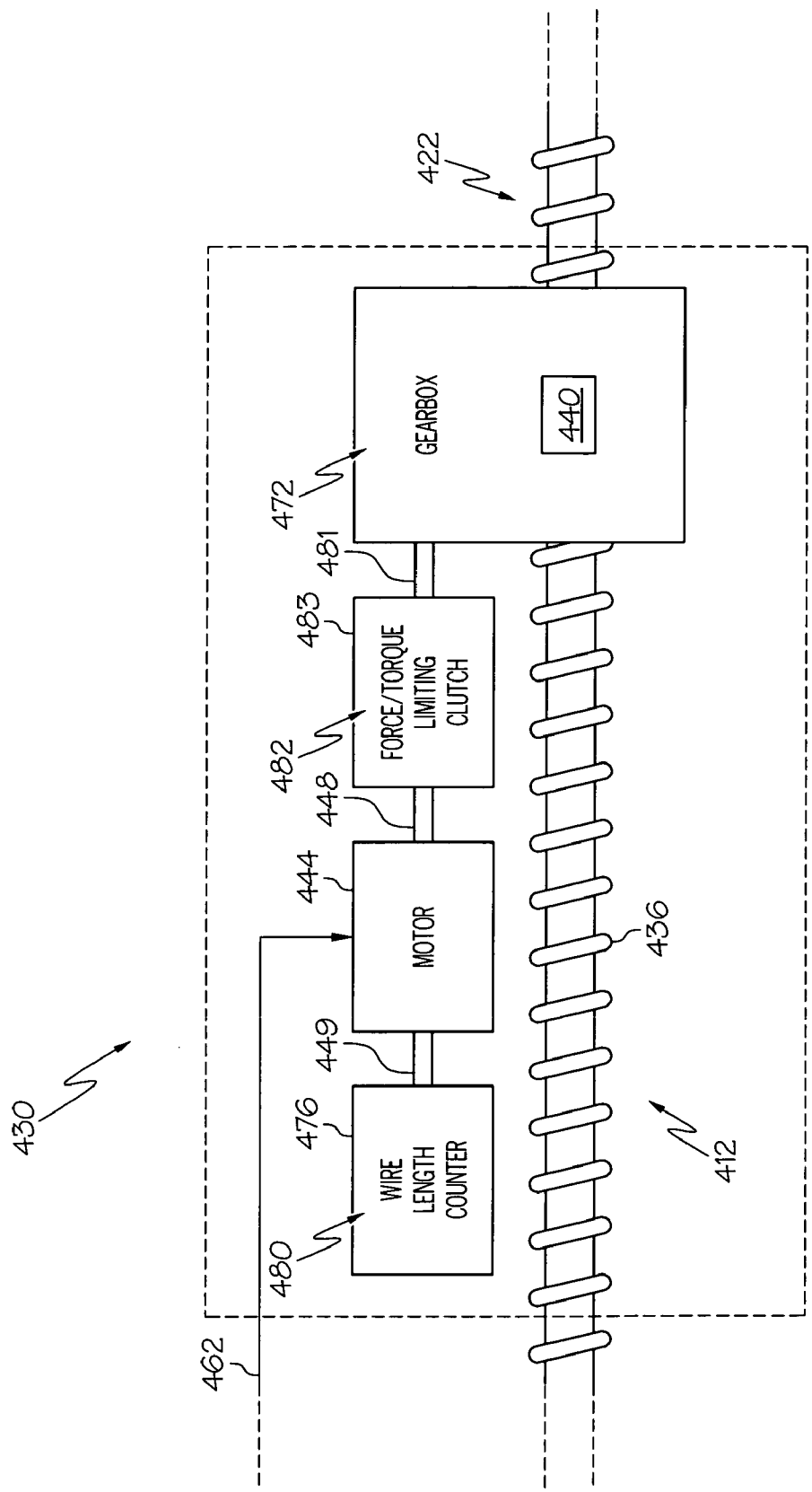
FIG. 16 is a schematic view of a particular embodiment of the mechanized guidewire drive assembly of FIG. 14 showing a wire length counter and a force/torque limiting clutch.

A fourth aspect of the invention is directed to a medical instrument having a catheter and a medical guidewire, an embodiment of which is shown in FIGS. 14-16. A first expression of the embodiment of FIGS. 14-16 is for a medical instrument 418 including a flexible catheter 424 and a medical guidewire 412. The catheter 424 has a distal end portion 417 which has a substantially bullet-nose shape, which is insertable into a body lumen of a patient, and which has at least one guidewire passageway opening 474. The medical guidewire 412 has a working portion 414 extendable beyond the at-least-one guidewire passageway opening 474.

A catheter distal end portion 417 having a substantially bullet-nose shape is a catheter distal end portion 417 with a cross section having a perimeter which has a shape of substantially a circle, wherein the circle continuously decreases in size as one moves toward the distal end 416, and wherein the distal end 416, as seen in a side-elevation view, is either rounded or flat. In one variation, the distal end portion 417 has a substantially hemispherical shape and the distal end 416 is rounded as seen in FIG. 14. In a different variation, not shown, the distal end portion has a substantially truncated conical shape and the distal end is flat. Other variations, including a substantially parabolic distal end portion, are left to the artisan.

In the broadest application of the first expression of the embodiment of FIGS. 14-16, as described in the second previous paragraph, the medical instrument 418 many have, but does not require a mechanized guidewire drive assembly 430, the medical guidewire 412 can be a loop-track or a non-loop-track medical guidewire, the medical guidewire 412 may have, but does not require, segments having different bending moment indices and/or different diameters (or other different cross-sectional shapes/sizes), and the medical guidewire 412 may have, but does not require, surface elevation features 434 such as external threads 436.

In one implementation of the first expression of the embodiment of FIGS. 14-16, the working portion 414 is extendable as a loop track beyond the at-least-one guidewire passageway opening 474. In one variation, the working portion 414 has a maximum loop-track length and includes first and second segments 420 and 422, wherein the first and second segments 420 and 422 together have a length greater than ninety percent of the maximum loop-track length, wherein the first segment 420 has a first bending moment of inertia and the second segment 422 has a second bending moment of inertia, and wherein the first bending moment of inertia is less than the second bending moment of inertia. In the same or a different variation, the medical instrument 418 includes a mechanized guidewire drive assembly 430, the working portion 414 includes first and second segments 420 and 422, the second segment 422 includes a repetitive series of spaced-apart surface elevation features 434 adapted for operable engagement with the mechanized guidewire drive assembly 430, and the mechanized guidewire drive assembly 430 includes a surface-elevation-feature engaging component 440 disposed within the catheter 424 toward the distal end 416. In one example, the surface elevation features 434 are external threads 436.

A second expression of the embodiment of FIGS. 14-16 is for a medical instrument 418 including a flexible catheter 424, a medical guidewire 412, and at least one wire length counter 476 and 478. The catheter 424 has a distal end 416 which is insertable into a body lumen of a patient. The medical guidewire 412 has a working portion 414 extendable beyond the distal end 416 of the catheter 424. The at-least-one wire length counter 476 and 478 is operatively connectable to the medical guidewire 412 to measure a length of the working portion 414 being extended beyond the distal end 416 of the catheter 424.

In the broadest application of the second expression of the embodiment of FIGS. 14-16, as described in the previous paragraph, the medical instrument 418 many have, but does not require a mechanized guidewire drive assembly 430, the medical guidewire 412 can be a loop-track or a non-loop-track medical guidewire, the medical guidewire 412 may have, but does not require, segments having different bending moment indices and/or different diameters (or other different cross-sectional shapes/sizes), and the medical guidewire 412 may have, but does not require, surface elevation features 434 such as external threads 436.

It is noted that a wire length counter 476 and 478 is any device which measures the extension length, from a reference position, of an extended wire, such devices being well known to those skilled in the art. It is also noted that the implementations, variations, examples, etc. of the first expression of the embodiment of FIGS. 14-16 are equally applicable to the second expression of the embodiment of FIGS. 14-16.

In one application of the second expression of the embodiment of FIGS. 14-16, the at-least-one wire length counter 476 and 478 includes a first wire length counter 476 operatively connectable to the second segment 422 to measure a length of the second segment 422 being extended beyond the distal end 416 of the catheter 424. In one variation, the at-least-one wire length counter 476 and 478 includes a second wire length counter 478 operatively connectable to the first segment 420 to measure a length of the first segment 420 being extended beyond the distal end 416 of the catheter 424. It is noted that this application and/or variation can be used with or without a mechanized guidewire drive assembly 430, as can be appreciated by the artisan. In one modification, wherein a mechanized guidewire drive assembly 430 is employed, the mechanized guidewire drive assembly 430 includes a motor 444 having a motor shaft 449, and the first wire length counter 476 includes an encoder 480 operatively connected to the motor shaft 449. In one enablement, not shown, the first and second wire length counters 476 and 478 include a display (such as a graphical or numerical display) on a console which is viewable by the clinician. In one extension, not shown, the catheter 424 includes length markings. In one example, a lead 462 supplies power to the motor 144.

A third expression of the embodiment of FIGS. 14-16 is for a medical instrument 418 including a flexible catheter 424, a medical guidewire 412, and a force/torque-limiting clutch 482. The catheter 424 has a distal end 416 insertable into a body lumen of a patient. The medical guidewire 412 includes a working portion 414 which is extendable beyond the distal end 416 of the catheter 424. The force/torque-limiting clutch 482 is operatively connectable to the medical guidewire 412.

In the broadest application of the third expression of the embodiment of FIGS. 14-16, as described in the previous paragraph, the medical instrument 418 many have, but does not require a mechanized guidewire drive assembly 430, the medical guidewire 412 can be a loop-track or a non-loop-track medical guidewire, the medical guidewire 412 may have, but does not require, segments having different bending moment indices and/or different diameters (or other different cross-sectional shapes/sizes), and the medical guidewire 412 may have, but does not require, surface elevation features 434 such as external threads 436. In one example, not shown, the medical guidewire is manually extended by the clinician and the force/torque-limiting clutch includes a force-limiting clutch. In another example, a mechanized guidewire drive assembly 430 is employed and includes a motor 444, wherein the motor 444 is a rotary motor, and wherein the force/torque-limiting clutch 482 is a torque-limiting clutch. Other examples are left to the artisan.

In one employment of the third expression of the embodiment of FIGS. 14-16, the medical instrument 418 also includes a mechanized guidewire drive assembly 430, wherein the medical guidewire 412 is adapted for operable engagement with the mechanized guidewire drive assembly 430, and wherein the mechanized guidewire drive assembly 430 includes the force/torque-limiting clutch 482. In one variation, the force/torque-limiting clutch 482 includes a slip clutch 483. In one modification, the mechanized guidewire drive assembly 430 includes a rotatable shaft (such as, but not limited to, a motor shaft 448) and a gearbox 472, wherein the gearbox 472 is adapted to operatively engage the medical guidewire 412, and wherein the slip clutch 483 is disposed between, and operatively connected to, the rotatable shaft (such as the motor shaft 448) and the gearbox 472. In one example, the mechanized guidewire drive assembly 430 includes a motor 444 operatively connected to the rotatable shaft (such as the motor shaft 448).

In one construction of the third expression of the embodiment of FIGS. 14-16, the slip clutch 483 of FIG. 16 includes a coupler (not shown) which is rotated by the flexible (in this construction) rotatable shaft (such as the motor shaft 448) and which includes six finger projections. The six finger projections surround a hexagonal output shaft 481 of the slip clutch 483. The coupler also includes a plurality of O-rings which surround, and apply a pressure against, the finger projections. When the moving medical guidewire 412 encounters a threshold resistance, the hexagonal output shaft 481 stops rotating and the rotating finger projections slip over the corners of the hexagonal output shaft 481. When the resistance encountered by the medical guidewire 412 falls below the threshold resistance, the rotating finger projections stay on the flats of the hexagonal output shaft 481. In this way, this construction of the slip clutch 483 interrupts the rotation of the hexagonal output shaft 481 when a threshold resistance is encountered, but allows rotation when the resistance falls below the threshold value. Other constructions of a slip clutch and/or a force/torque-limiting clutch 482 are left to the artisan.

Medical Instrument Having a Guidewire and Articulated Catheter

Figure 17:
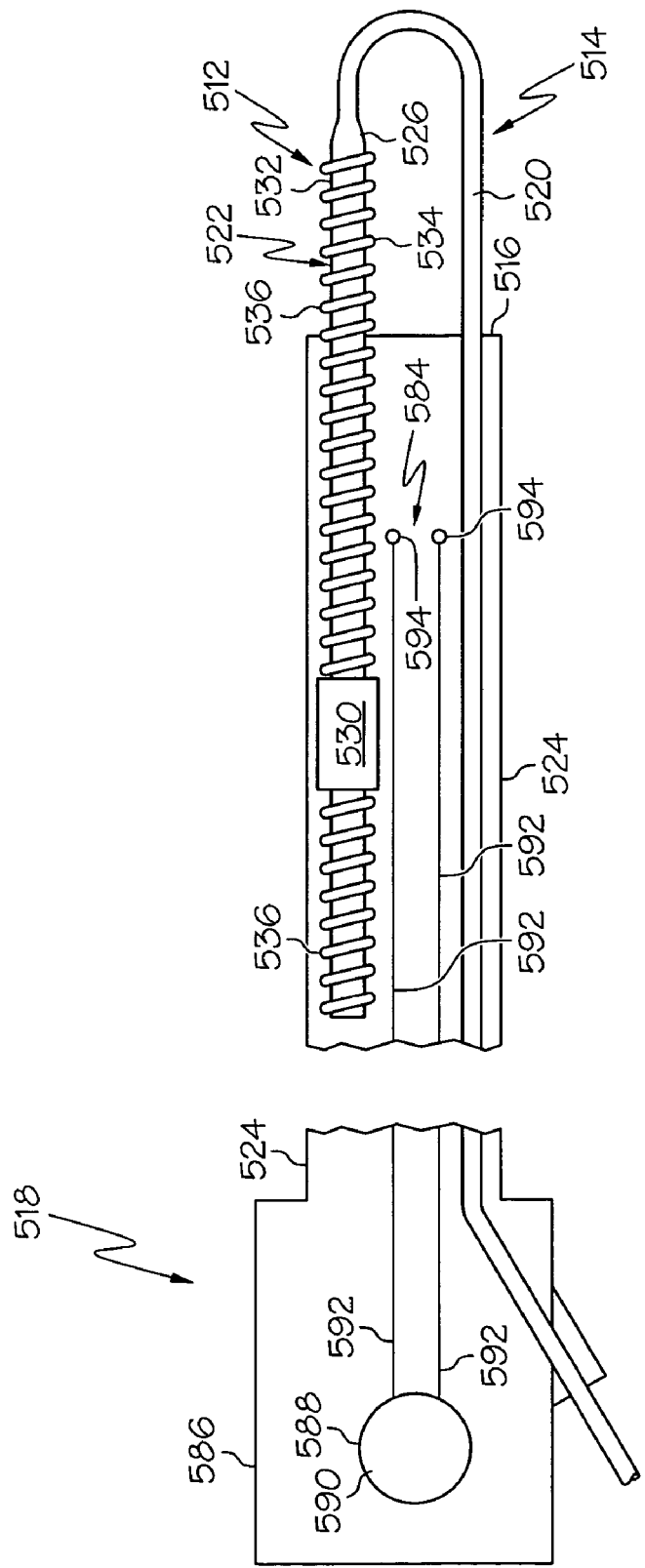
FIG. 17 is a schematic side-elevational cutaway view of a fourth embodiment of a medical instrument of the invention including an articulated catheter and a medical guidewire.
Figure 18:
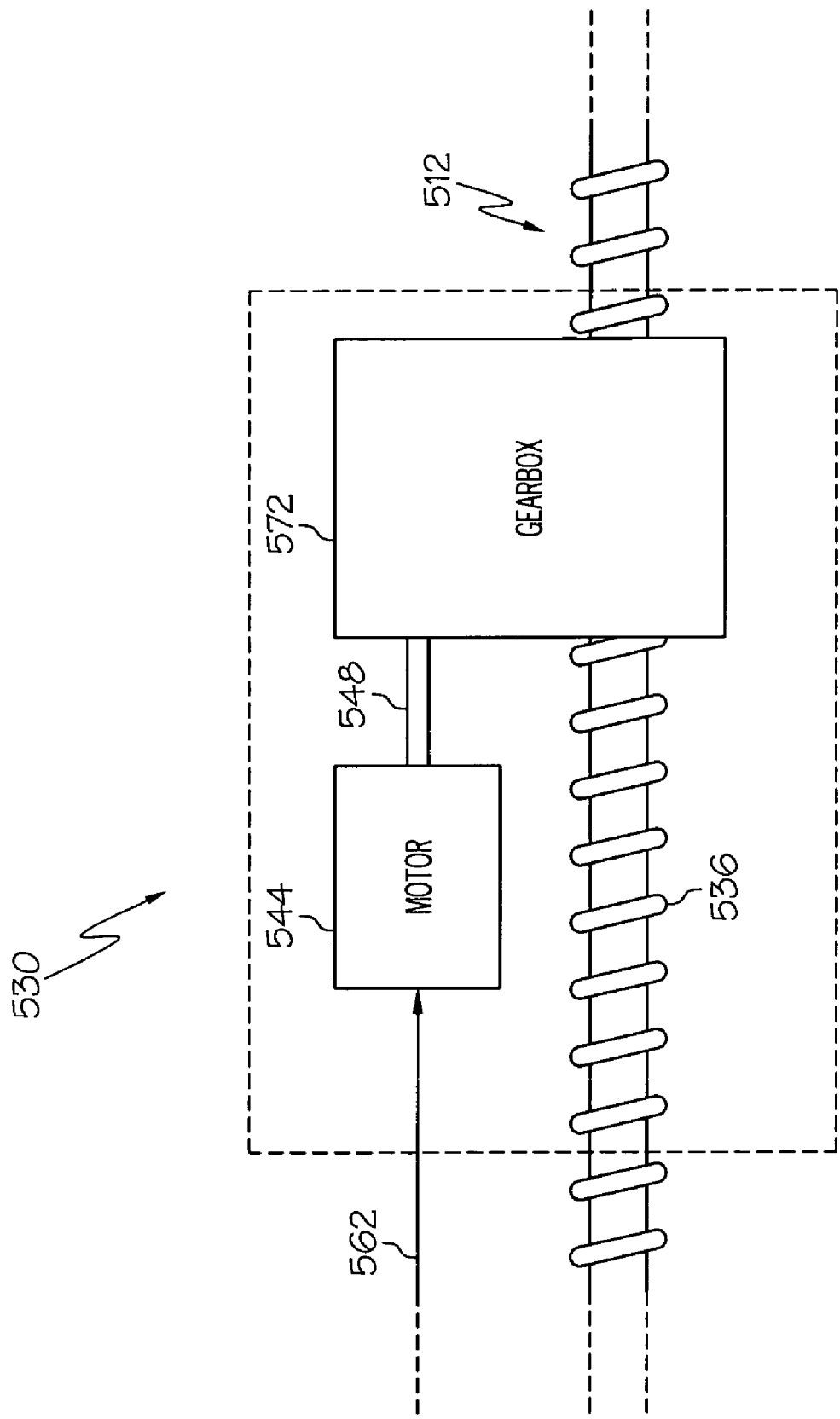
FIG. 18 is a schematic view of a particular embodiment of the mechanized guidewire drive assembly of FIG. 17 including a motor and a gearbox, wherein it is noted that the motor is disposed in the catheter.

A fifth aspect of the invention is directed to a medical instrument having a guidewire and articulated catheter, a first embodiment of which is shown in FIGS. 17-18. A first expression of the embodiment of FIGS. 17-18 is for a medical instrument 518 including a flexible catheter 524 and a medical guidewire 512. The catheter 524 has a distal end 516 and an articulated section 584 insertable into a body lumen of a patient, wherein the articulated section 584 is adapted to be controlled from outside the body lumen. The medical guidewire 512 includes a working portion 514 which is extendable as a loop track beyond the distal end 516 of the catheter 524. The working portion 514 has a maximum loop-track length and includes first and second segments 520 and 522 together having a length greater than ninety percent of the maximum loop-track length. The first segment 520 has a first bending moment of inertia and the second segment 522 has a second bending moment of inertia. The first bending moment of inertia is less than the second bending moment of inertia.

In the broadest application of the first expression of the embodiment of FIGS. 17-18, as described in the previous paragraph, the medical instrument 518 many have, but does not require a mechanized guidewire drive assembly 530, and the medical guidewire 512 may have, but does not require, surface elevation features 534 such as external threads 536.

In one arrangement of the first expression of the embodiment of FIGS. 17-18, the articulated section 584 is disposed toward (and in one example proximate) the distal end 516. In one variation, the medical instrument 518 includes a handle 586 having a control input device 588, wherein the handle 586 is connected to the catheter 524, and wherein the control input device 588 is operatively connected to the articulated section 584. Examples of control input devices include, without limitation, rotatable control knobs, control switches, and control buttons. In one modification, the control input device 588 includes a control knob 590 and the medical instrument 518 includes two control cables 592 each having one end connected to a corresponding anchor point 594 in the articulated section 584 and each having the other end operatively connected to the control knob 590, wherein rotation of the control knob 590 bends the articulated section 584 in one direction and counter-rotation of the control knob 590 bends the articulated section 584 in the opposite direction, as can be appreciated by those skilled in the art. Other mechanisms for bending the articulated section 584 are left to the artisan. In one application, the catheter 524 is an insertion tube of a flexible endoscope (with the endoscope imager, working channel, etc. omitted from FIGS. 17-18 for clarity).

A second expression of the embodiment of FIGS. 17-18 is for a medical instrument 518 including a flexible catheter 524, a mechanized guidewire drive assembly 530, and a medical guidewire 512. The catheter 524 has a distal end 516 and an articulated section 584 insertable into a body lumen of a patient, wherein the articulated section 584 is adapted to be controlled from outside the body lumen. The medical guidewire 512 includes a working portion 514 which is extendable as a loop track beyond the distal end 516 of the catheter 524. The working portion 514 includes an exterior surface 532 having a repetitive series of spaced-apart surface elevation features 534 adapted for operable engagement with the mechanized guidewire drive assembly 530.

In one arrangement of the second expression of the embodiment of FIGS. 17-18, the articulated section 584 is disposed toward (and in one example proximate) the distal end 516. In one variation, the medical instrument 518 includes a handle 586 having a control input device 588, wherein the handle 586 is connected to the catheter 524, and wherein the control input device 588 is operatively connected to the articulated section 584.

In one enablement of the second expression of the embodiment of FIGS. 17-18, the working portion 514 includes first and second segments 520 and 522 wherein the surface elevation features 534 are present on the second segment 522 and are absent from the first segment 520. In one variation, the working portion 514 has a maximum loop-track length, and the first and second segments 520 and 522 together have a length greater than ninety percent of the maximum loop-track length. In this variation, the first segment 520 has a first bending moment of inertia and the second segment 522 has a second bending moment of inertia, wherein the first bending moment of inertia is less than the second bending moment of inertia.

A third expression of the embodiment of FIGS. 17-18 is for a medical instrument 518 including a flexible catheter 524, a mechanized guidewire drive assembly 530, and a medical guidewire 512. The catheter 524 has a distal end 516 and an articulated section 584 insertable into a body lumen of a patient, wherein the articulated section 584 is adapted to be controlled from outside the body lumen. The medical guidewire 512 includes a working portion 514 which is extendable as a loop track beyond the distal end 516 of the catheter 524. The working portion 514 includes an exterior surface 532 having external threads 536 adapted for operable engagement with the mechanized guidewire drive assembly 530.

The arrangements, enablements, etc. of the previously described second expression of the embodiment of FIGS. 17-18 are equally applicable to the third expression of the embodiment of FIGS. 17-18, wherein the surface elevation features 534 of such second expression are the external threads 536 of such third expression. In one modification, the working portion 514 includes a third segment 526 extending from the second segment 522 to the first segment 520, wherein the third segment 526 has a length and has a varying third diameter which is substantially equal to the second diameter (of the second segment 522) proximate the second segment 522 and which is substantially equal to the first diameter (of the first segment 520) proximate the first segment 520.

In one enablement of the third expression of the embodiment of FIGS. 17-18, the mechanized guidewire drive assembly 530 includes a motor 544 disposed within the catheter 524. In one variation, a lead 562 supplies power to the motor 544, and the motor 544 rotates a motor shaft 548 which is operatively connected to a gearbox 572 which is operatively connectable to the medical guidewire 512. In the same or a different enablement, the catheter 524 is an insertion tube of a flexible endoscope.

Figure 19:
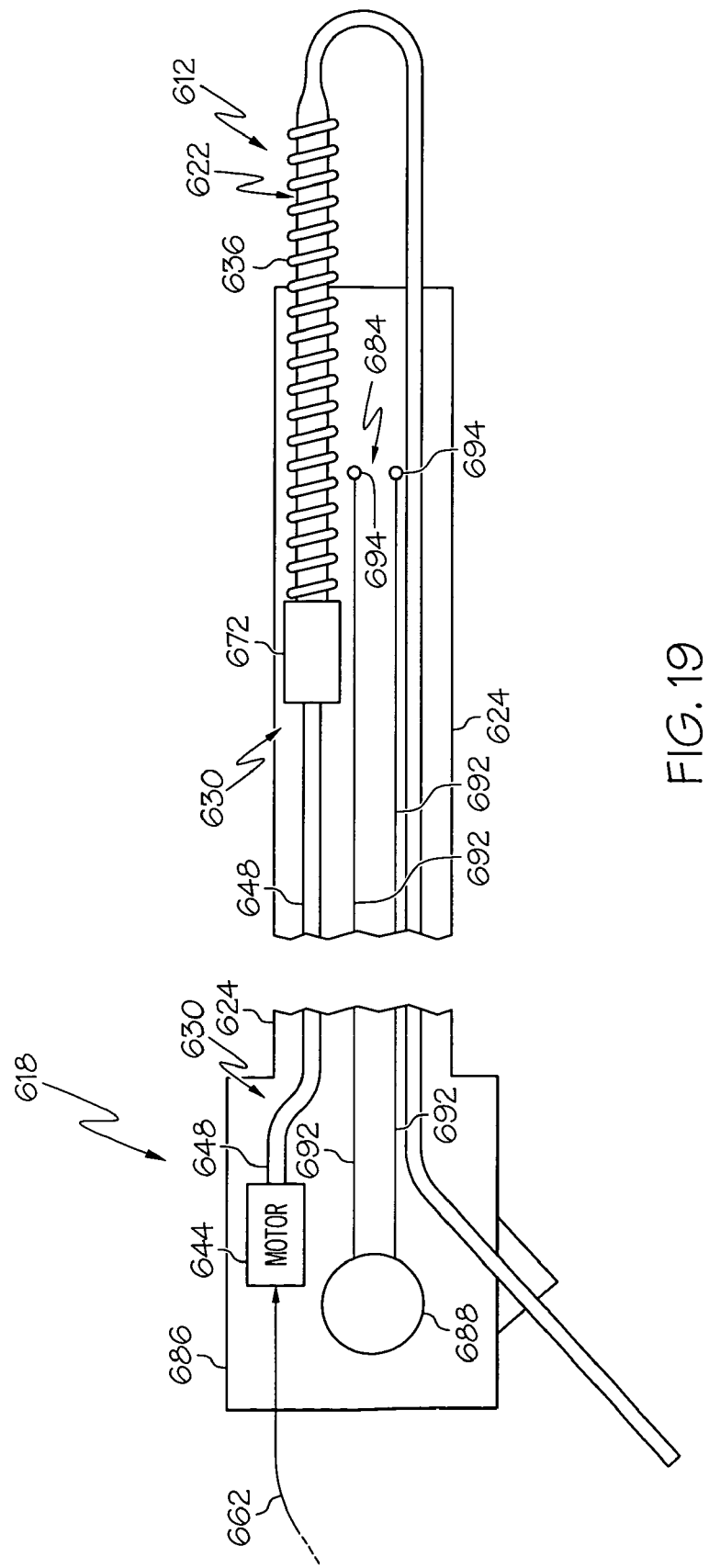
FIG. 19 is a schematic side-elevational cutaway view of a fifth embodiment of a medical instrument of the invention including an articulated catheter and a medical guidewire, wherein the motor of the mechanized guidewire drive assembly of the medical instrument is disposed in the handle of the medical instrument, and wherein the portion of the second segment (including the external threads thereof) of the medical guidewire extending proximal of the gearbox has been omitted for clarity.

A second embodiment of the fifth aspect of the invention is shown in FIG. 19, wherein the portion of the second segment 622 (including the external threads 636 thereof) of the medical guidewire 612 extending proximal of the gearbox 672 has been omitted for clarity but would look like the gearbox/guidewire arrangement shown in FIG. 18. The embodiment of the medical instrument 618 of FIG. 19 is identical to the embodiment of the medical instrument 518 of FIGS. 17-18 except that the motor 644 of the mechanized guidewire drive assembly 630 is disposed in the handle 686, instead of in the catheter 624, and except that a longer flexible motor shaft 648 operatively connects the motor 644 to the gearbox 672. The articulated section 684, the control input device 688, the control cables 692, the anchor points 694, and the lead 662 supplying power to the motor 644 also are shown in FIG. 19.

Figure 20:
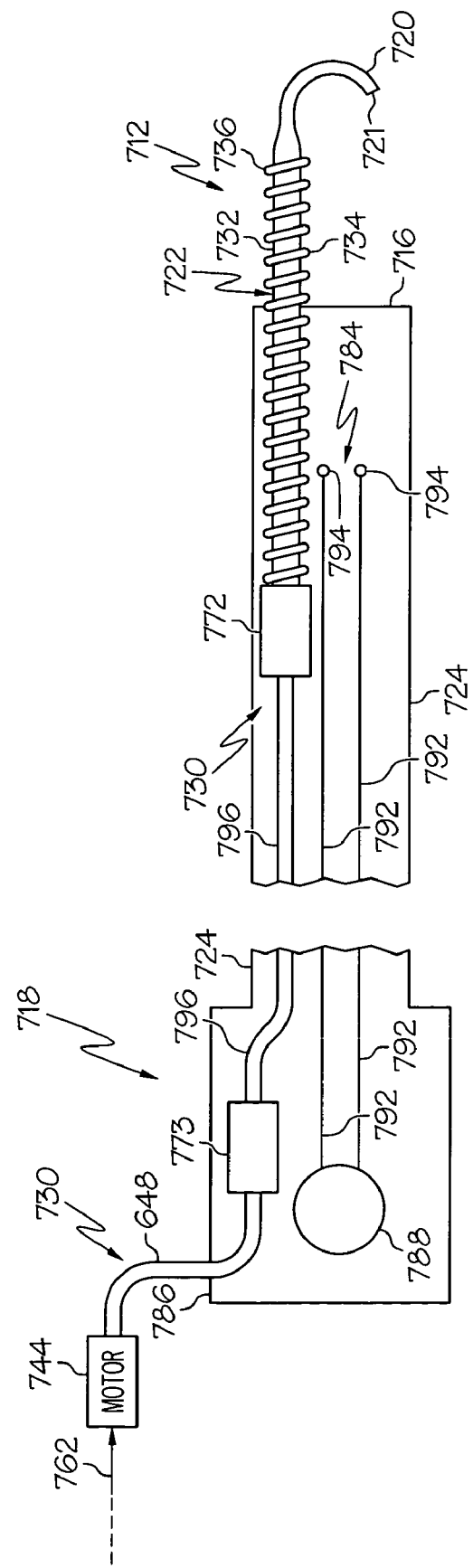
FIG. 20 is a schematic side-elevational cutaway view of a sixth embodiment of a medical instrument of the invention including an articulated catheter and a medical guidewire, wherein the motor of the mechanized guidewire drive assembly of the medical instrument is disposed outside the handle and the catheter of the medical instrument, and wherein the portion of the second segment (including the external threads thereof) of the medical guidewire extending proximal of the gearbox has been omitted for clarity.

A third embodiment of the fifth aspect of the invention is shown in FIG. 20, wherein the portion of the second segment 722 (including the external threads 736 thereof) of the medical guidewire 712 extending proximal of the gearbox 772 has been omitted for clarity but would look like the gearbox/guidewire arrangement shown in FIG. 18. The embodiment of the medical instrument 718 of FIG. 20 is identical to the embodiment of the medical instrument 518 of FIGS. 17-18 except that the medical guidewire 712, when fully extended, has a free end 721 extending beyond the distal end 716, except that the motor 744 of the mechanized guidewire drive assembly 730 is disposed outside the handle 786 and the catheter 724, except that a second gearbox 773 is disposed in the handle 786, except that a long flexible motor shaft 648 operatively connects the motor 744 to the second gearbox 773, and except that a connecting shaft 796 operatively connects the second gearbox 773 to the first gearbox 772. The articulated section 784, the control input device 788, the control cables 792, the anchor points 794, and the lead 762 supplying power to the motor 744 also are shown in FIG. 20.

A first expression of the embodiment of FIG. 20 is for a medical instrument 718 including a flexible catheter 724 and a medical guidewire 712. The catheter 724 has a distal end 716 and an articulated section 784 insertable into a body lumen of a patient, wherein the articulated section 784 is adapted to be controlled from outside the body lumen. The medical guidewire 712 is extendable beyond the distal end 716 of the catheter 724. The medical guidewire 712 includes first and second segments 720 and 722. The first segment 720 has a first bending moment of inertia and the second segment 722 has a second bending moment of inertia, wherein the first bending moment of inertia is less than the second bending moment of inertia. The first segment 720 has a free end 721 which extends beyond the distal end 716 of the catheter 724 when the medical guidewire 712 is fully extended.

In the broadest application of the first expression of the embodiment of FIG. 20, as described in the previous paragraph, the medical instrument 718 many have, but does not require a mechanized guidewire drive assembly 730, and the medical guidewire 712 may have, but does not require, surface elevation features 734 such as external threads 736.

A second expression of the embodiment of FIG. 20 is for a medical instrument 718 including a flexible catheter 724, a mechanized guidewire drive assembly 730, and a medical guidewire 712. The catheter 724 has a distal end 716 and an articulated section 784 insertable into a body lumen of a patient, wherein the articulated section 784 is adapted to be controlled from outside the body lumen. The medical guidewire 712 is extendable beyond the distal end 716 of the catheter 724. The medical guidewire 712 includes an exterior surface 732 having a repetitive series of spaced-apart surface elevation features 734 adapted for operable engagement with the mechanized guidewire drive assembly 730. The medical guidewire 712 has a free end 721 which extends beyond the distal end 716 of the catheter 724 when the medical guidewire 712 is fully extended.

A third expression of the embodiment of FIG. 20 is for a medical instrument 718 including a flexible catheter 724, a mechanized guidewire drive assembly 730, and a medical guidewire 712. The catheter 724 has a distal end 716 and an articulated section 784 insertable into a body lumen of a patient, wherein the articulated section 784 is adapted to be controlled from outside the body lumen. The medical guidewire 712 is extendable beyond the distal end 716 of the catheter 724. The medical guidewire 712 includes an exterior surface 732 having external threads 736 adapted for operable engagement with the mechanized guidewire drive assembly 730. The medical guidewire 712 has a free end 721 which extends beyond the distal end 716 of the catheter 724 when the medical guidewire 712 is fully extended.

Medical Instrument Having a Guidewire and an Add-To Catheter

A sixth aspect of the invention is directed to a medical instrument having a guidewire and an add-to catheter, a first embodiment of which is shown in FIGS. 21-24. A first expression of the embodiment of FIGS. 21-24 is for a medical instrument 818 including a flexible catheter 824 and a medical guidewire 812. The catheter 824 has a distal end 816 insertable into a body lumen of a patient, and the catheter 824 is adapted to slidably receive a rail-coupling portion 800 of an adjunct medical device 801. The medical guidewire 812 includes a working portion 814 which is extendable as a loop track beyond the distal end 816 of the catheter 824. The working portion 814 has a maximum loop-track length and includes first and second segments 820 and 822 together having a length greater than ninety percent of the maximum loop-track length. The first segment 820 has a first bending moment of inertia and the second segment 822 has a second bending moment of inertia. The first bending moment of inertia is less than the second bending moment of inertia.

In the broadest application of the first expression of the embodiment of FIGS. 20-24, as described in the previous paragraph, the medical instrument 818 many have, but does not require a mechanized guidewire drive assembly 830, and the medical guidewire 812 may have, but does not require, surface elevation features 834 such as external threads 836.

Examples of adjunct medical devices 801 include, without limitation, a second medical instrument 802 such as a medical instrument not having a medical guidewire and, as shown in the alternate embodiment of FIG. 25 (wherein like reference numerals refer to like components in FIGS. 24 and 25), a connector 803 adapted to slidably receive a rail-coupling portion of a second medical instrument 802 such as a medical instrument not having a medical guidewire. Other examples are left to the artisan. In one choice of materials, the connector consists essentially of Polytetrafluoroethylene (PTFE). In one implementation, the PTFE reduces sliding friction.

In one construction of the first expression of the embodiment of FIGS. 20-24, the catheter 824 includes a rail 804, wherein the rail 804 is adapted for couplingly and slidably receiving the rail-coupling portion 800 of the adjunct medical device 801. In one variation, the rail 804 is a monolithic portion of the catheter 824. In one choice of materials, the catheter 824 consists essentially of polyurethane. In another variation, not shown, the rail is releasably attachable to the catheter. In one modification, the rail 804 is disposed on an exterior surface of the catheter 824. In another modification, not shown, the rail is disposed on an interior surface of the catheter. In one design, the rail 804 includes a plurality of transversely extending notches 805 (see FIGS. 21-22 and especially the detailed laid-open view of the rail 804 in FIG. 23). In one implementation, the notches 805 provide flexibility.

In one application of the first expression of the embodiment of FIGS. 20-24, the catheter 824 is an insertion tube of a flexible endoscope (with the endoscope imager, working channel, etc. omitted from FIGS. 21-24 for clarity), and the adjunct medical device 801 includes a working channel 806 adapted for receiving a medical appliance 807. In one variation, the working channel 807 is the interior of a flexible annular tube 808 whose exterior surface is adapted to couple to, and slide along, the rail 804. In one example, the coupling engagement is provided by a matching tongue-and-groove arrangement. In a different application, not shown, the working channel is absent, and the medical appliance itself is adapted to couple to, and slide along, the rail. Examples of medical appliances 807 include, without limitation, imagers, irrigators, cutting blades, ultrasound end effectors, wire snares, etc. In one modification, not shown, the catheter includes two or more rails.

It is noted that the catheter 824 of the first expression of the embodiment of FIGS. 21-14 can be described as an add-to catheter, allowing for a small catheter diameter, which, with the medical guidewire 812, allows for easier of insertion into the body lumen of a patient. This is followed by adding an adjunct medical device 801 to the catheter 824, as needed, for a particular medical procedure. Successive adjunct medical devices can be brought to the treatment site, used as medically desired, and withdrawn from the patient with the catheter 824 acting as a guide rail for the adjunct medical devices and remaining at the treatment site until completion of the medical procedure.

A second expression of the embodiment of FIGS. 21-24 is for a medical instrument 818 including a flexible catheter 824, a mechanized guidewire drive assembly 830, and a medical guidewire 812. The catheter 824 has a distal end 816 insertable into a body lumen of a patient, and the catheter 824 is adapted to slidably receive a rail-coupling portion 800 of an adjunct medical device 801. The medical guidewire 812 includes a working portion 814 which is extendable as a loop track beyond the distal end 816 of the catheter 824. The working portion 814 includes an exterior surface 832 having a repetitive series of spaced-apart surface elevation features 834 adapted for operable engagement with the mechanized guidewire drive assembly 830.

In one construction of the second expression of the embodiment of FIGS. 20-24, the catheter 824 includes a rail 804, wherein the rail 804 is adapted for couplingly and slidably receiving the rail-coupling portion 800 of the adjunct medical device 801. In one variation, the rail 804 includes a plurality of transversely extending notches 805. In one application of the first expression of the embodiment of FIGS. 20-24, the catheter 824 is an insertion tube of a flexible endoscope, and the adjunct medical device 801 includes a working channel 806 adapted for receiving a medical appliance 807.

In one enablement of the second expression of the embodiment of FIGS. 21-24, the working portion 814 includes first and second segments 820 and 822 wherein the surface elevation features 834 are present on the second segment 822 and are absent from the first segment 820. In one variation, the working portion 814 has a maximum loop-track length, and the first and second segments 820 and 822 together have a length greater than ninety percent of the maximum loop-track length. In this variation, the first segment 820 has a first bending moment of inertia and the second segment 822 has a second bending moment of inertia, wherein the first bending moment of inertia is less than the second bending moment of inertia.

In one example of the second expression of the embodiment of FIGS. 21-24, the surface elevation features 834 are external threads 836. In one modification, the working portion 814 includes a third segment 826 extending from the second segment 822 to the first segment 820, wherein the third segment 826 has a length and has a varying third diameter which is substantially equal to the second diameter (of the second segment 822) proximate the second segment 822 and which is substantially equal to the first diameter (of the first segment 820) proximate the first segment 820.

It is noted that the constructions, applications, etc. of the first expression of the embodiment of FIGS. 21-24 are equally applicable to the second expression of the embodiment of FIGS. 21-24. In one enablement of the second expression of the embodiment of FIGS. 21-24, the mechanized guidewire drive assembly 830 includes a motor 844 disposed within the catheter 824.

A second embodiment of the sixth aspect of the invention is shown in FIGS. 26-27. A first expression of the embodiment of FIGS. 26-27 is for a medical instrument 918 including a flexible catheter 924 and a medical guidewire 912. The catheter 924 has a distal end 916 insertable into a body lumen of a patient, and the catheter 924 is adapted to slidably receive a rail-coupling portion 900 of an adjunct medical device 901. The medical guidewire 912 is extendable beyond the distal end 916 of the catheter 924. The medical guidewire 912 includes first and second segments 920 and 922. The first segment 920 has a first bending moment of inertia and the second segment 922 has a second bending moment of inertia, wherein the first bending moment of inertia is less than the second bending moment of inertia. The first segment 920 has a free end 921 which extends beyond the distal end 916 of the catheter 924 when the medical guidewire 912 is fully extended.

In the broadest application of the first expression of the embodiment of FIGS. 26-27, as described in the previous paragraph, the medical instrument 918 many have, but does not require a mechanized guidewire drive assembly 930, and the medical guidewire 912 may have, but does not require, surface elevation features 934 such as external threads 936. In one construction of the first expression of the embodiment of FIGS. 26-27, the catheter 924 includes a rail 904 adapted for couplingly and slidably receiving the rail-coupling portion 900 of the adjunct medical device 901.

A second expression of the embodiment of FIGS. 26-27 is for a medical instrument 918 including a flexible catheter 924, a mechanized guidewire drive assembly 930, and a medical guidewire 912. The catheter 924 has a distal end 916, and the catheter 924 is adapted to slidably receive a rail-coupling portion 900 of an adjunct medical device 901. The medical guidewire 912 is extendable beyond the distal end 916 of the catheter 924. The medical guidewire 912 includes an exterior surface 932 having a repetitive series of spaced-apart surface elevation features 934 adapted for operable engagement with the mechanized guidewire drive assembly 930. The medical guidewire 912 has a free end 921 which extends beyond the distal end 916 of the catheter 924 when the medical guidewire 912 is fully extended. In one construction of the second expression of the embodiment of FIGS. 26-27, the catheter 924 includes a rail 904 adapted for couplingly and slidably receiving the rail-coupling portion 900 of the adjunct medical device 901.

A third expression of the embodiment of FIGS. 26-27 is for a medical instrument 918 including a flexible catheter 924, a mechanized guidewire drive assembly 930, and a medical guidewire 912. The catheter 924 has a distal end 916, and the catheter 924 is adapted to slidably receive a rail-coupling portion 900 of an adjunct medical device 901. The medical guidewire 912 is extendable beyond the distal end 916 of the catheter 924. The medical guidewire 912 includes an exterior surface 932 having external threads 936 adapted for operable engagement with the mechanized guidewire drive assembly 930. The medical guidewire 912 has a free end 921 which extends beyond the distal end 916 of the catheter 924 when the medical guidewire 912 is fully extended. In one construction of the third expression of the embodiment of FIGS. 26-27, the catheter 924 includes a rail 904 adapted for couplingly and slidably receiving the rail-coupling portion 900 of the adjunct medical device 901.

Several benefits and advantages are obtained from one or more of the expressions and embodiments of the invention. In one application, having a medical instrument with an articulated catheter and with a loop-track or non-loop-track guidewire including a first segment having a bending moment of inertia less than that of a second segment allows easier extension of the first segment in a body lumen of a patient followed by easier extension and temporary anchoring of the second segment and easier advancement of the catheter, as can be appreciated by the artisan. In the same or a different application, having a medical instrument with an articulated catheter and with a loop-track or non-loop-track guidewire including an exterior surface having a repetitive series of spaced-apart surface elevation features, such as external threads, allows operable engagement thereof with a mechanized guidewire drive assembly for improved guidewire extension and catheter advancement, as can be appreciated by those skilled in the art. In one employment which utilizes a mechanized guidewire drive assembly, when the surface-elevation-feature engaging component of the mechanized guidewire drive assembly is located proximate the distal end of the catheter (insertion tube) of a flexible endoscope, there is less tendency for the catheter to "loop" within the colon and cause pain to the patient during a colonoscopy.

While the present invention has been illustrated by a description of several expressions, embodiments, methods, and examples, etc. thereof, it is not the intention of the applicants to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A medical instrument comprising:
    a) a flexible catheter having a distal end and an articulated section insertable into a body lumen of a patient, wherein the articulated section is adapted to be articulately controlled from outside the body lumen;
    b) a mechanized guidewire drive assembly; and
    c) a medical guidewire including a working portion which is extendable as a loop track beyond the distal end of the catheter, wherein the working portion includes an exterior surface having a repetitive series of spaced-apart surface elevation features adapted for operable engagement with the mechanized guidewire drive assembly to non-rotatably extend and retract the medical guidewire, and wherein the medical guidewire is devoid of any medical-treatment component.

2. The medical instrument of claim 1, wherein the articulated section is disposed toward the distal end.

3. The medical instrument of claim 2, also including a handle having a control input device, wherein the handle is connected to the catheter, and wherein the control input device is operatively connected to the articulated section.

4. The medical instrument of claim 3, wherein the working portion includes first and second segments, and wherein the spaced-apart surface elevation features are present on the second segment and are absent from the first segment.

5. The medical instrument of claim 4, wherein the working portion has a maximum loop-track length, wherein the first and second segments together have a length greater than ninety percent of the maximum loop-track length, wherein the first segment has a first bending moment of inertia and the second segment has a second bending moment of inertia, and wherein the first bending moment of inertia is less than the second bending moment of inertia.

6. The medical instrument of claim 3, wherein the mechanized guidewire drive assembly includes a motor disposed within the catheter.

7. The medical instrument of claim 3, wherein the mechanized guidewire drive assembly includes a gearbox disposed within the catheter.

8. A medical instrument comprising:
    a) a flexible catheter having a distal end and an articulated section insertable into a body lumen of a patient, wherein the articulated section is adapted to be controlled from outside the body lumen;
    b) a mechanized guidewire drive assembly; and
    c) a medical guidewire including a working portion which is extendable as a loop track beyond the distal end of the catheter, wherein the working portion includes an exterior surface having a repetitive series of spaced-apart surface elevation features adapted for operable engagement with the mechanized guidewire drive assembly, wherein the articulated section is disposed toward the distal end, also including a handle having a control input device, wherein the handle is connected to the catheter, wherein the control input device is operatively connected to the articulated section, wherein the working portion includes first and second segments, and wherein the surface elevation features are present on the second segment and are absent from the first segment.

9. The medical instrument of claim 8, wherein the working portion has a maximum loop-track length, wherein the first and second segments together have a length greater than ninety percent of the maximum loop-track length, wherein the first segment has a first bending moment of inertia and the second segment has a second bending moment of inertia, and wherein the first bending moment of inertia is less than the second bending moment of inertia.

10. A medical instrument comprising:
    a) a flexible catheter having a distal end and an articulated section insertable into a body lumen of a patient, wherein the articulated section is adapted to be controlled from outside the body lumen;
    b) a mechanized guidewire drive assembly; and c) a medical guidewire including a working portion which is extendable as a loop track beyond the distal end of the catheter, wherein the working portion includes an exterior surface having a repetitive series of spaced-apart surface elevation features adapted for operable engagement with the mechanized guidewire drive assembly, wherein the surface elevation features are external threads.

11. The medical instrument of claim 10, wherein the articulated section is disposed toward the distal end.

12. The medical instrument of claim 11, also including a handle having a control input device, wherein the handle is connected to the catheter, and wherein the control input device is operatively connected to the articulated section.

13. The medical instrument of claim 12, wherein the mechanized guidewire drive assembly includes a motor disposed within the catheter.

14. The medical instrument of claim 10, wherein the working portion includes first and second segments, and wherein the external threads are present on the second segment and are absent from the first segment.

15. The medical instrument of claim 12, wherein the mechanized guidewire drive assembly includes a gearbox disposed within the catheter.

16. The medical instrument of claim 15, wherein the working portion has a maximum loop-track length, wherein the first and second segments together have a length greater than ninety percent of the maximum loop-track length, wherein the first segment has a first bending moment of inertia and the second segment has a second bending moment of inertia, and wherein the first bending moment of inertia is less than the second bending moment of inertia.

17. The medical instrument of claim 16, wherein the working portion includes a third segment extending from the second segment to the first segment, and wherein the third segment has a length and has a varying third diameter which is substantially equal to the second diameter proximate the second segment and which is substantially equal to the first diameter proximate the first segment.

18. The medical instrument of claim 10, wherein the catheter is an insertion tube of a flexible endoscope.

19. A medical instrument comprising:
a) a flexible catheter having a distal end and an articulated section insertable into a body lumen of a patient, wherein the articulated section is adapted to be articulatably controlled from outside the body lumen;
b) a mechanized guidewire drive assembly; and
c) a medical guidewire which is extendable beyond the distal end of the catheter, wherein the medical guidewire includes an exterior surface having a repetitive series of spaced-apart surface elevation features adapted for operable engagement with the mechanized guidewire drive assembly to non-rotatably extend and retract the medical guidewire, wherein the medical guidewire is devoid of any medical-treatment component, and wherein the medical guidewire has a free end which extends beyond the distal end of the catheter when the medical guidewire is fully extended.

20. The medical instrument of claim 19, wherein the surface elevation features are external threads.

* * * * *